(12) United States Patent
Kimura et al.

(10) Patent No.: US 6,353,750 B1
(45) Date of Patent: Mar. 5, 2002

(54) LIVING BODY INSPECTING APPARATUS AND NONINVASIVE BLOOD ANALYZER USING THE SAME

(75) Inventors: Rokusaburo Kimura; Kaoru Asano; Hideo Kusuzawa, all of Kobe; Yasuhiro Kouchi, Kakogawa; Toshiyuki Ozawa, Himezi, all of (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/403,551

(22) PCT Filed: Jun. 24, 1998

(86) PCT No.: PCT/JP98/02875

§ 371 Date: Oct. 25, 1999

§ 102(e) Date: Oct. 25, 1999

(87) PCT Pub. No.: WO99/00053

PCT Pub. Date: Jan. 7, 1999

(30) Foreign Application Priority Data

Jun. 27, 1997 (JP) ............................... 9-172216
Dec. 2, 1997 (JP) ............................... 9-331924

(51) Int. Cl.⁷ ................................................ A61B 5/00
(52) U.S. Cl. ........................ 600/344; 600/310; 600/322
(58) Field of Search ................................. 600/322–324, 600/309–310, 326, 328, 344, 318, 316, 340, 334–335, 473, 476, 479; 356/39, 41

(56) References Cited

U.S. PATENT DOCUMENTS

| | | | | |
|---|---|---|---|---|
| 4,898,175 A | * | 2/1990 | Noguchi ..................... | 600/476 |
| 5,209,230 A | * | 5/1993 | Swedlow et al. ........... | 600/322 |
| 5,226,417 A | * | 7/1993 | Swedlow et al. ........... | 600/336 |
| 5,348,003 A | * | 9/1994 | Caro ........................... | 600/310 |
| 5,368,025 A | * | 11/1994 | Young et al. ............... | 600/310 |
| 5,413,101 A | * | 5/1995 | Sugiura ...................... | 600/323 |
| 5,551,422 A | * | 9/1996 | Simonsen et al. .......... | 600/322 |
| 5,553,613 A | * | 9/1996 | Parker ........................ | 600/316 |
| 5,974,338 A | * | 11/1999 | Asano et al. ............... | 600/323 |
| 6,061,583 A | * | 5/2000 | Ishihara et al. ............ | 600/322 |

FOREIGN PATENT DOCUMENTS

| | | |
|---|---|---|
| JP | 2-61309 | 5/1990 |
| JP | 3-39005 | 4/1991 |
| JP | 3-88505 | 9/1991 |
| JP | 4-51936 | 2/1992 |
| JP | 6-503728 | 4/1994 |
| JP | 6-125881 | 5/1994 |
| JP | 6-505903 | 7/1994 |
| JP | 7-88105 | 4/1995 |
| JP | 7-213498 | 8/1995 |
| WO | 92/03965 | 9/1992 |
| WO | 92/16142 | 9/1992 |
| WO | 9216142 A1 | 10/1992 |

* cited by examiner

*Primary Examiner*—Eric F. Winakur
*Assistant Examiner*—Matthew Kremer

(57) ABSTRACT

The purpose is to fix a portion of a living body, which is an object of measurement, stably without strain and to acquire accurate inspection results with good reproducibility. An apparatus for capturing an image of a living body includes: a base for mounting a portion of a living body to be inspected; two sidewall members capable of holding the mounted portion of the living body therebetween from both sides; a light source section for supplying a light to the portion of the living body held on the base and between the sidewall members; and a light receiving section for detecting optical information from the portion of the living body supplied with the light, and a non-invasive apparatus for living body inspection including the above apparatus for capturing an image of a living body in which the light receiving section includes an image capturing element, and an analyzing section for calculating information on blood flowing through a blood vessel by analyzing an image of a tissue including the blood vessel obtained by the image capturing element.

25 Claims, 33 Drawing Sheets

LIVING BODY INSPECTING APPARATUS AND NONINVASIVE BLOOD ANALYZER USING THE SAME

This application is the national phase under 35 U.S.C. § 371 of PCT International Application No. PCT/JP98/02875 which has an International filing date of Jun. 24, 1998, which designated the United States of America.

BACKGROUND OF THE INVENTION

1. Field of the Invention

The present invention relates to an apparatus for living body inspection and a non-invasive blood analyzer using the same, and particularly to an apparatus for transcutaneously detecting optical information from a tissue including a blood vessel of a portion of a living body and an apparatus for analyzing the detected optical information to acquire information on blood, for example, hemoglobin concentration or hematocrit.

2. Description of the Related Art

For such an apparatus for living body inspection, an apparatus is known in which a human finger is inserted into a groove of a finger accepting device, the finger is deformed by pressing it with a roller until the outline of the finger is fitted to a cross-sectional shape of the groove, and the deformed finger is irradiated with light to detect a transmitted light therefrom (for example, see Japanese Unexamined Patent Publication No. HEI 06-503728).

However, in such a conventional apparatus, the finger is extended linearly and pressed strongly in the groove, so that the blood vessel or tissue is deformed to cause a congestive state or ischemic state. This raises a problem that it is not possible to obtain optical information from a blood vessel or tissue in a normal state.

The present invention has been made in consideration of the above-described situation and it is an object of the present invention to provide an apparatus for living body inspection and a non-invasive blood analyzer using the same in which it is possible to acquire normal optical information by holding a portion of the living body stably without applying an excessive correcting force or pressing force.

SUMMARY OF THE INVENTION

The present invention provides an apparatus for living body inspection comprising: a base for mounting a portion of a living body to be inspected; sidewall members capable of holding the mounted portion of the living body therebetween from both sides; a light source section for supplying a light to the portion of the living body held on the base and between the sidewall members; and a light receiving section for detecting optical information from the portion of the living body supplied with the light.

In this apparatus for living body inspection, the base has a morphology that conforms, for example, to a palm of a hand of a human being and its plural fingers and its thumb, and the sidewall members position one of the plural fingers and the thumb appropriately relative to the light source section and the light receiving section.

Further, the present invention provides an apparatus for living body inspection wherein the light receiving section comprises an image capturing element. Further, the present invention provides a non-invasive apparatus for living body inspection comprising: an analyzing section for calculating information on blood flowing through a blood vessel by analyzing an image of a tissue including the blood vessel obtained by an image capturing element of an apparatus for living body inspection; and an outputting section for outputting the calculated information.

DETAILED DESCRIPTION OF THE PREFERRED EMBODIMENT

Figure 1:
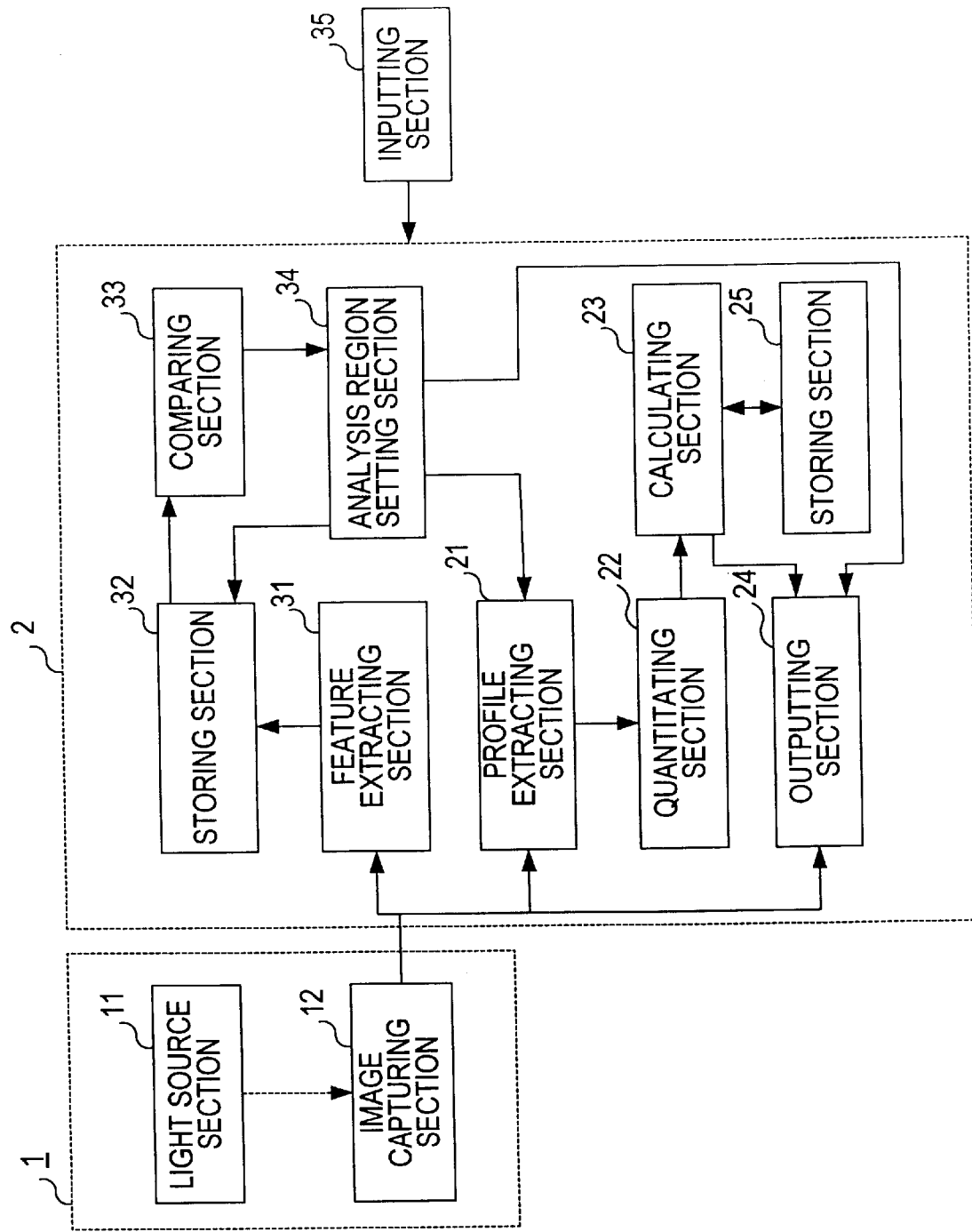
FIG. 1 is a block diagram showing a construction of a detecting section and an analyzing section in a first embodiment of the present invention.

In an apparatus for living body inspection according to the present invention, the living body designates a mammalian animal including a human being, a rabbit, a dog, a cat, a rat, and a mouse, and a portion of the living body designates not a tissue separated from the living body but a portion of a tissue of the living body as it is, which is, for example, a finger or a toe in the case of human beings and a tail in the case of other animals.

Preferably, in the present invention, the portion of the living body mounted on the base is elastically held between the sidewall members from both sides thereof with a suitable pressure. This is because, if the portion of the living body is fixed by squeezing or deforming it too strongly, the blood vessel is pressed to generate a congestive state or ischemic state, making it impossible to obtain an accurate inspection result. Also, this is because the portion of the living body can be mounted stably at the center of the base even if the thickness of the portion of the living body is different. Also, in order to mount the portion of the living body on the base in a more natural state, the base for mounting the portion of the living body is preferably formed so that at least a part of a surface of the base is fitted to a morphology of the portion of the living body to be mounted.

For example, when the portion of the living body to be inspected is a finger or thumb of a human hand, the base preferably has a surface shape made of a curved surface which is conformable to a curved surface formed by the plural fingers and the thumb including the finger or thumb to be inspected and a palm that has the fingers and the thumb; and the sidewall members preferably protrude from the base so that the sidewall members hold the finger or thumb to be inspected therebetween from both sides when the plural fingers, the thumb and the palm are mounted on the base so that they conform to the above curved surface. Further, the base preferably includes at least one recess for positioning the finger or thumb to be inspected on an upper surface thereof, and more preferably includes three recesses. Namely, the fingers, the thumb, and the palm can be more stably mounted on the base by providing, on the base, also recesses for respectively positioning plural fingers and/or the thumb.

Also, the sidewall members are preferably urged to approach each other and to hold the portion of the living body therebetween.

This can be achieved, for example, by providing, on the base, a supporting member for supporting the sidewall members on both sides so that the sidewall members are movable to approach each other and an urging member for urging the sidewall members on both sides so that the sidewall members approach each other.

In this case, the supporting member preferably has a sliding mechanism or a hinge mechanism, and the urging member preferably comprises a member like a spring.

Also, the sidewall members are preferably urged to generate a force component which presses the portion of the living body toward the base with the sidewall members holding the portion of the living body therebetween.

In the case where the portion of the living body to be inspected is a tail of an animal, the base preferably has a surface shape that fits to the morphology of the tail, and the sidewall members preferably hold the mounted tail therebetween to such an extent that they are not deformed or pressed. In this case, the base desirably includes at least one recess that positions the tail.

Also, in the apparatus for living body inspection, bases and sidewall members with plural kinds of sizes may be prepared in accordance with the size of the portion of the living body. For example, in the case where the portion of the living body is a finger or thumb of a human hand, three kinds each for an infant, a child, and an adult may be prepared. At this time, it is advantageous to have a structure such that the base and the sidewall members are disposed to be capable of being easily detached from the other constituent members.

The light source section may employ a semiconductor laser (hereinafter, LD) or a LED (Light Emitting Diode) or a halogen light source, and it may be applied to the portion of the living body directly or via a fiber. The wavelength of the light source is preferably within a range of 600 to 950 nm which can be transmitted through a tissue of a living body and where light absorption by water is not large.

The light receiving section may be constructed with an optical system such as a lens and a light receiving element such as a photodiode or a CCD (Charge Coupled Device).

An image capturing element such as a CCD is preferably used as the light receiving element in order to obtain information on density distribution of a blood vessel portion in detail. Instead of a CCD, a line sensor or a photodiode array may be used. Further, the information on density distribution can also be obtained by scanning a single photodiode in a direction traversing a blood vessel.

The optical system of the light receiving section may be constituted simply by using only a lens for TV (for example, BD1214D manufactured by COMICAR) if an image capturing element such as a CCD is used as the light receiving element.

The apparatus of the present invention may further comprise a cover member, and the cover member may cover an upper part of the portion of the living body held by the sidewall members. In this case, the light source section may be disposed in the cover member and the light receiving section may be disposed below the base, whereby the light receiving section is placed so as to receive the light transmitted through the portion of the living body from the light source via an opening disposed in the base.

Also, the non-invasive blood analyzer of the present invention includes an analyzing section for calculating information on blood flowing through a blood vessel by analyzing an image including the blood vessel obtained by the above apparatus for living body inspection in which the light receiving section comprises an image capturing element. Here, the information on blood is information on blood or blood stream, and is specifically a blood component concentration, a blood vessel diameter, or the like.

The above analyzing section may be constructed with a personal computer.

The non-invasive blood analyzer of the present invention may further include a judging section for judging a mounting state of the portion of the living body relative to the base on the basis of the image obtained by the apparatus for living body inspection, and an outputting section for outputting an instruction message based on the judged mounting state.

Also, the non-invasive blood analyzer of the present invention may further include a light quantity controlling section for controlling a quantity of the light of the light source section on the basis of the obtained image.

The present invention is now detailed based on embodiments shown by the drawings as follows. The present invention is not limited thereby.

FIRST EMBODIMENT

FIG. 1 is a block diagram showing a construction of a first embodiment of a non-invasive blood analyzer employing an apparatus for living body inspection of the present invention. Referring to FIG. 1, a detecting section 1 serving as the apparatus for living body inspection is provided with a light source section 11 for irradiating a portion of the living body (a middle finger of a hand of a human being in this case) including a blood vessel and an image capturing section 12 for capturing an optical image (image of transmitted light in this case) of the irradiated portion of the living body. In other words, the detecting section 1 in this case is an apparatus for capturing an image of the living body.

An analyzing section 2 is provided with a feature extracting section 31 for extracting a positional feature of a portion of the living body (coordinates of a recess in an outline of a joint portion of a finger in this case) in each captured image when the image capturing section 12 captures an image of the portion of the living body timesequentially by a plural number of times, a storing section 32 for storing the respective extracted features, a comparing section 33 for comparing the respective features, and an analysis region setting section 34 for setting an analysis region including the same blood vessel portion in the plurality of images based on a result of comparison.

Further, the analyzing section 2 is provided with a profile extracting section 21 for extracting an image density distribution at a portion linearly traversing a blood vessel orthogonally in the analysis region as an image density profile with respect to the captured image, a quantitating section 22 for quantitating a morphological feature of the extracted density profile, a calculating section 23 for calculating a blood vessel diameter, a blood component concentration, and the like based on the quantitated feature, a storing section 25 for storing a result of calculation and an outputting section (CRT) 24 for outputting the result of calculation or a monitored image.

Incidentally, an inputting section 35 comprises a keyboard and a mouse and carries out setting of a measurement mode, initial setting of the analysis region, inputting of calculation conditions of the calculating section 23 and so on. Further, the analyzing section 2 is constructed with a personal computer.

Figure 2:
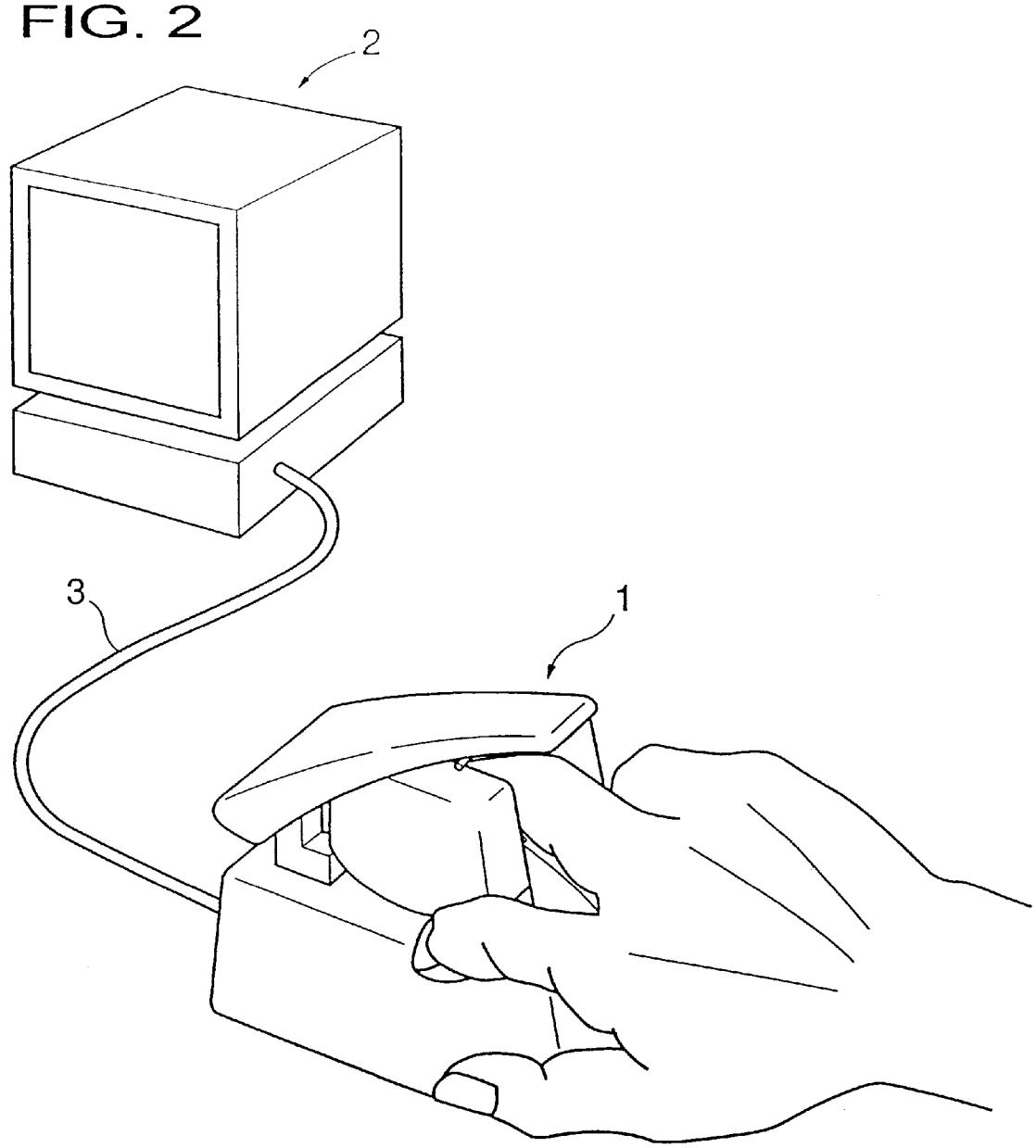
FIG. 2 is a perspective view showing an outlook of the detecting section and the analyzing section in the first embodiment of the present invention.

FIG. 2 is a perspective view of an outlook of the apparatus shown in FIG. 1 where the detecting section 1 and the analyzing section 2 are connected by a signal cable 3.

Figure 3:
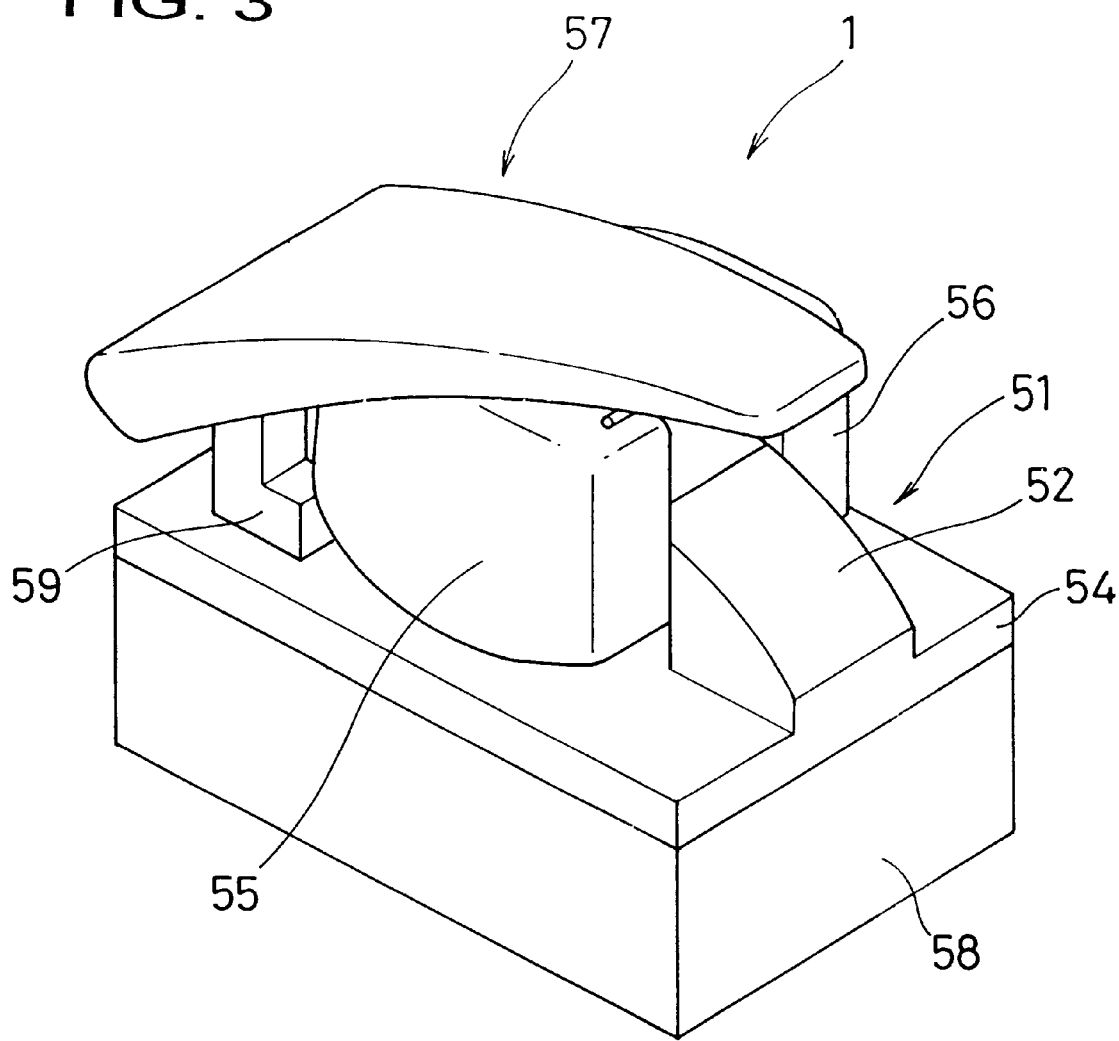
FIG. 3 is a perspective view showing the detecting section of the first embodiment of the present invention.
Figure 7:
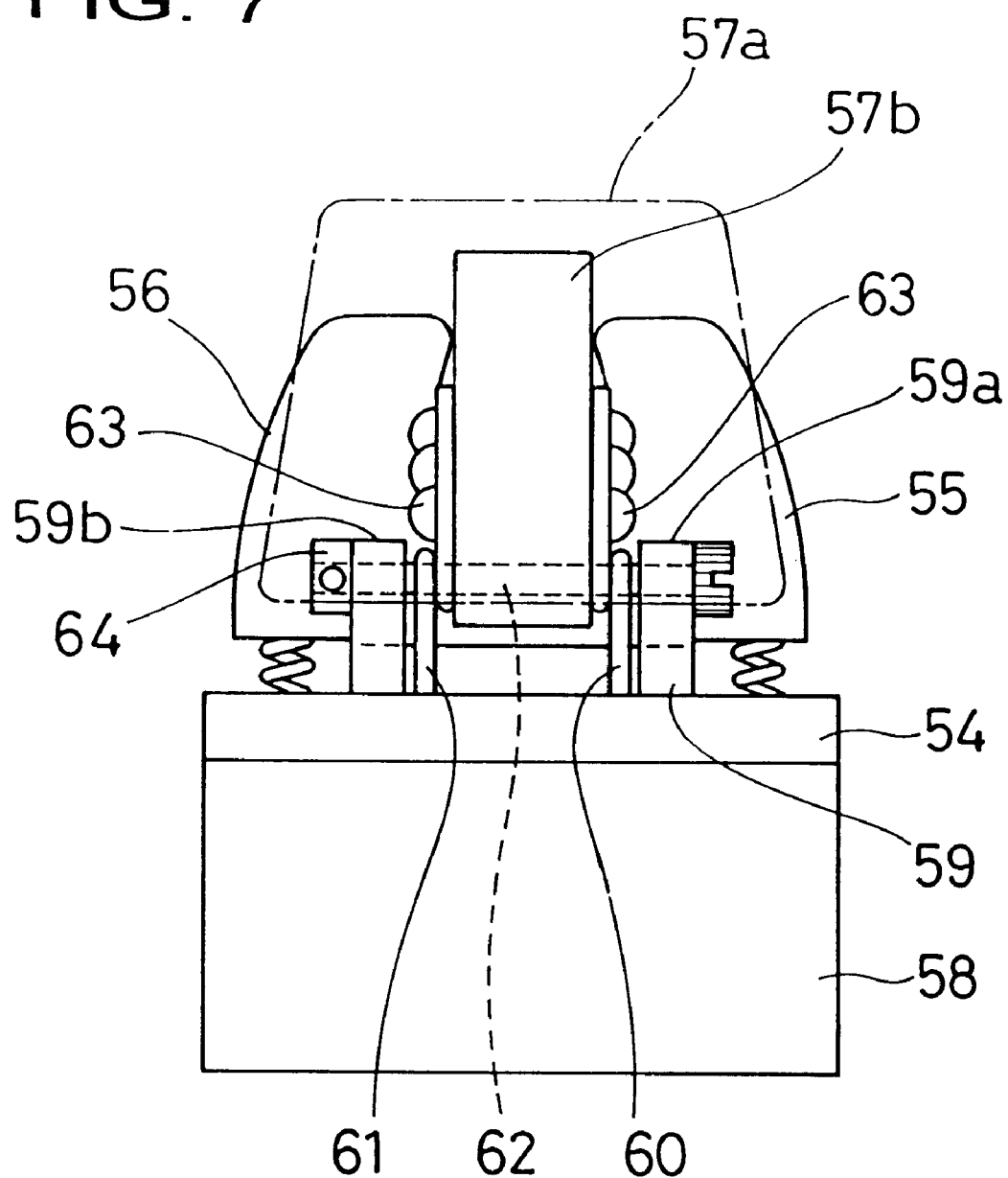
FIG. 7 is a rear view of the detecting section of the first embodiment of the present invention.
Figure 8:
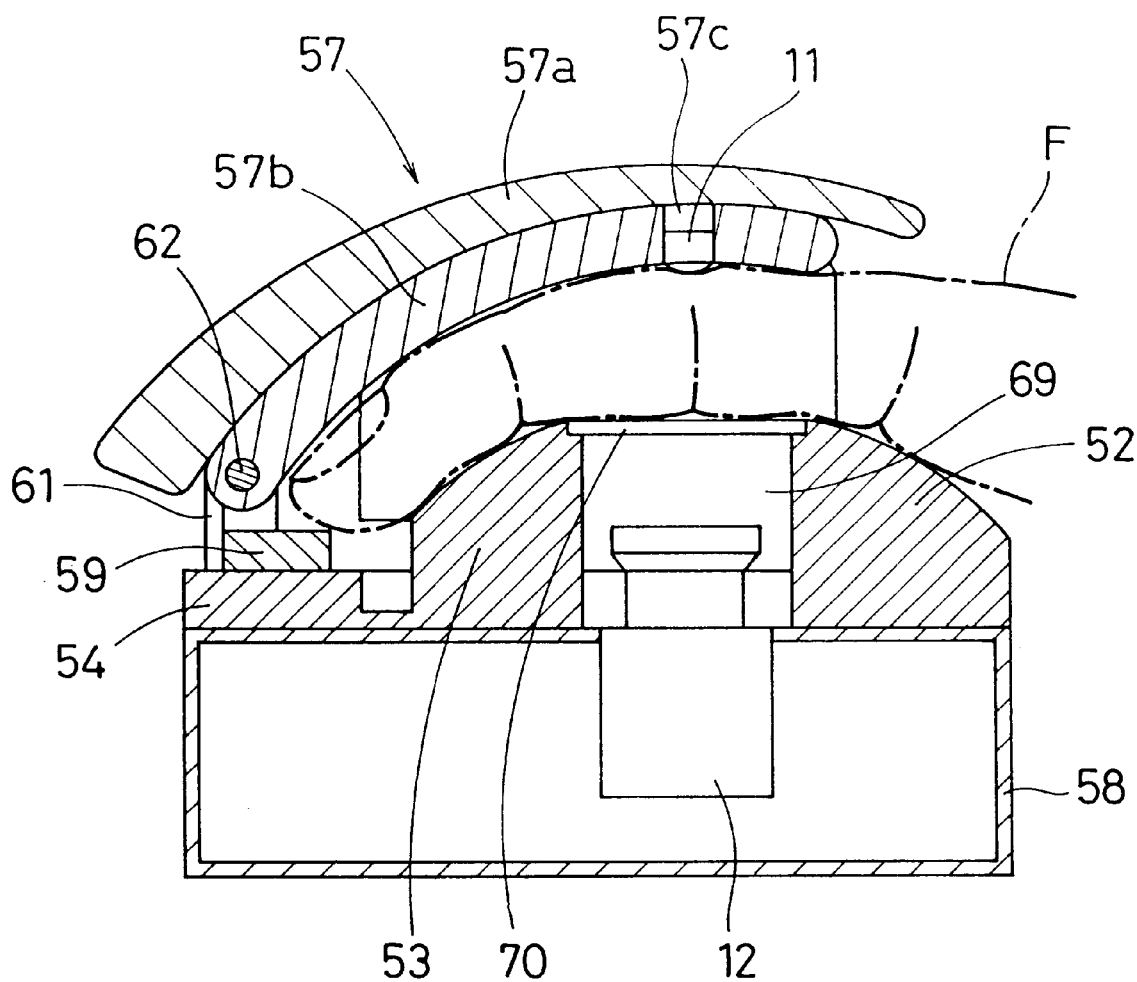
FIG. 8 is a cross-sectional view of the detecting section of the first embodiment of the present invention as viewed in the direction of the arrows along the line X—X of FIG. 4.
Figure 9:
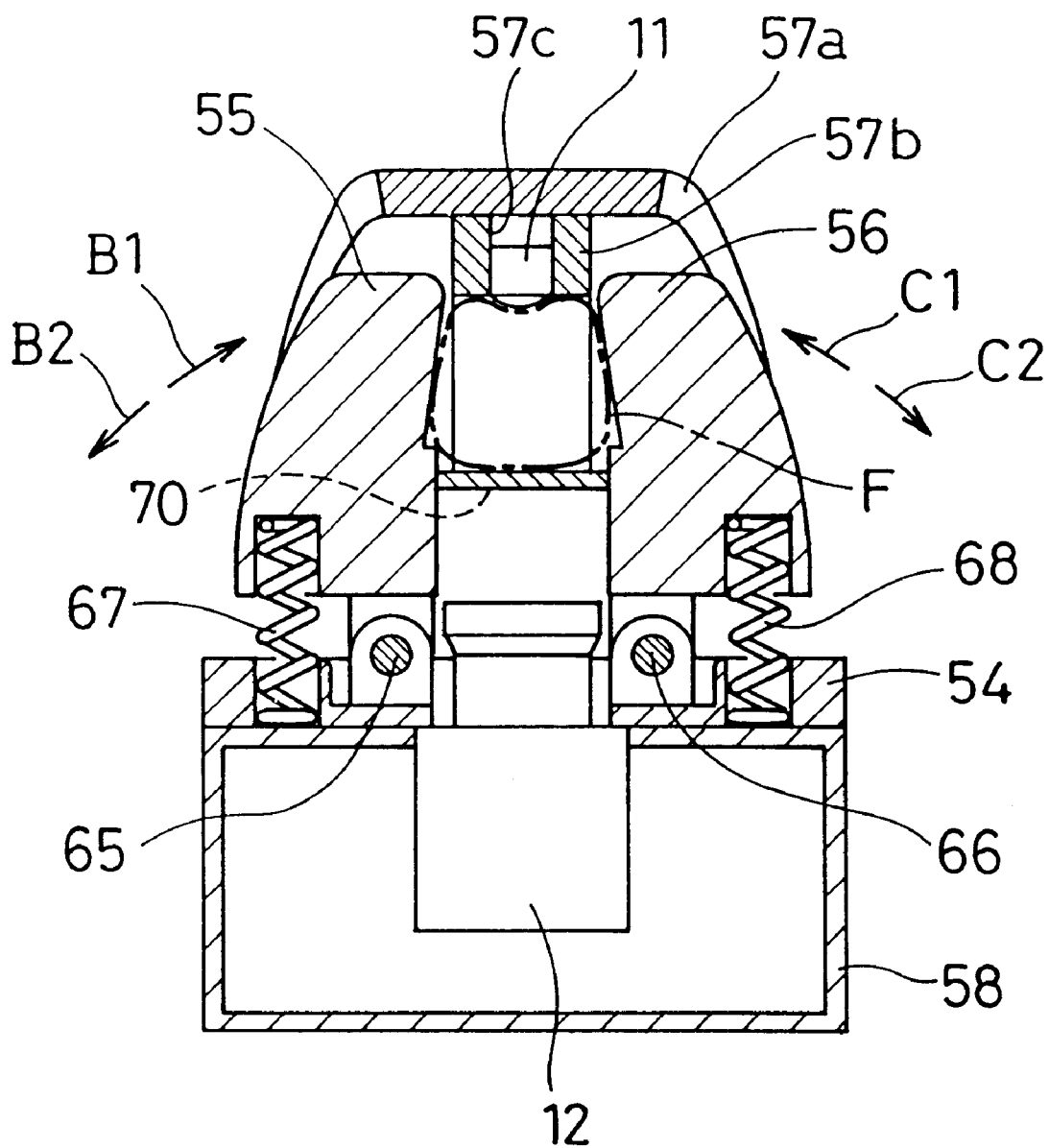
FIG. 9 is a cross-sectional view of the detecting section of the first embodiment of the present invention as viewed in the direction of the arrows along the line Y—Y of FIG. 4.
Figure 10:
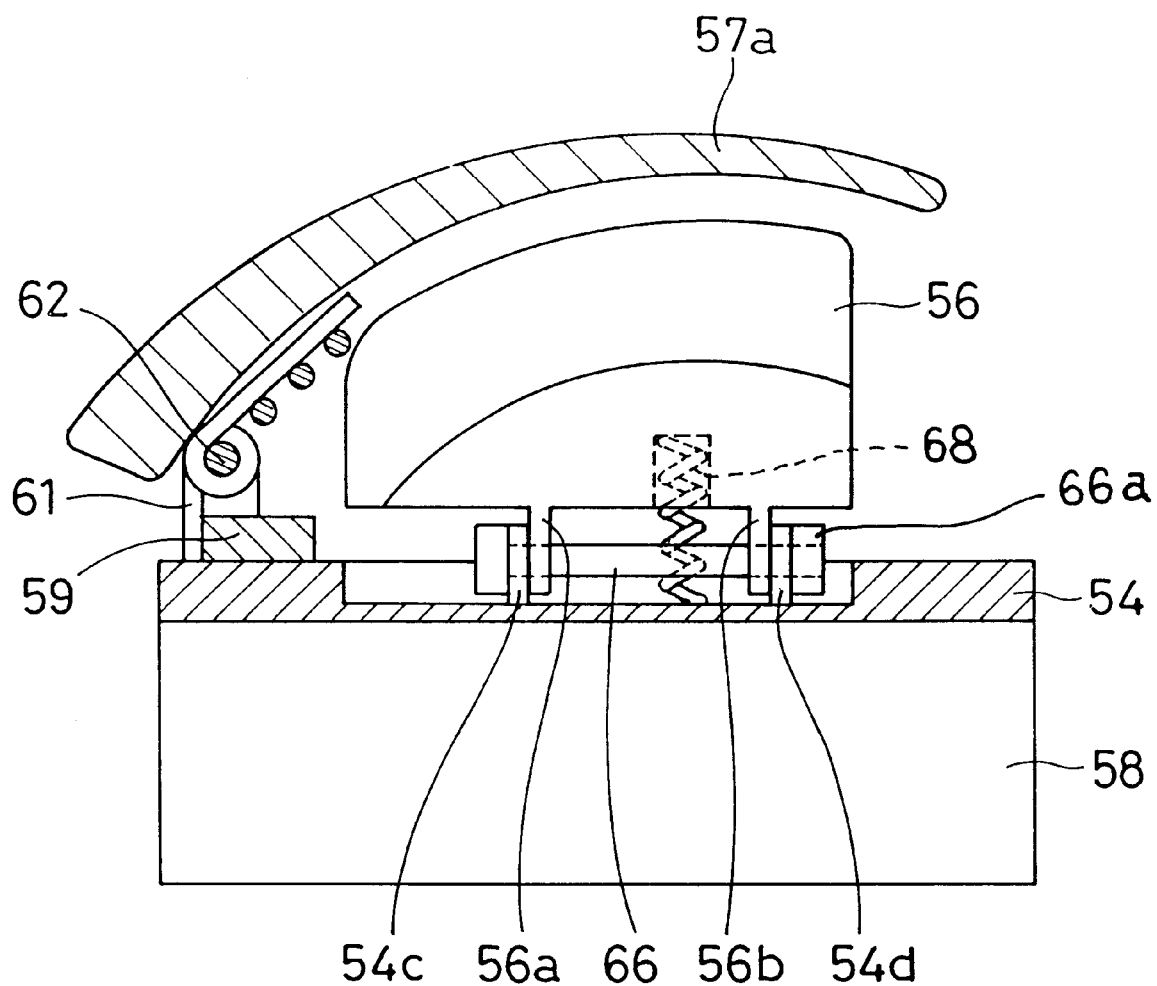
FIG. 10 is a cross-sectional view of the detecting section of the first embodiment of the present invention as viewed in the direction of the arrows along the line Z—Z of FIG. 4.

FIG. 3 is a perspective view showing the detecting section 1. FIGS. 4 to 7 are a plan view, a front view, a side view, and a rear view showing the detecting section 1, respectively. FIGS. 8 to 10 are cross-sectional views taken along the lines X—X, Y—Y, and Z—Z in FIG. 4, respectively.

Figure 6:
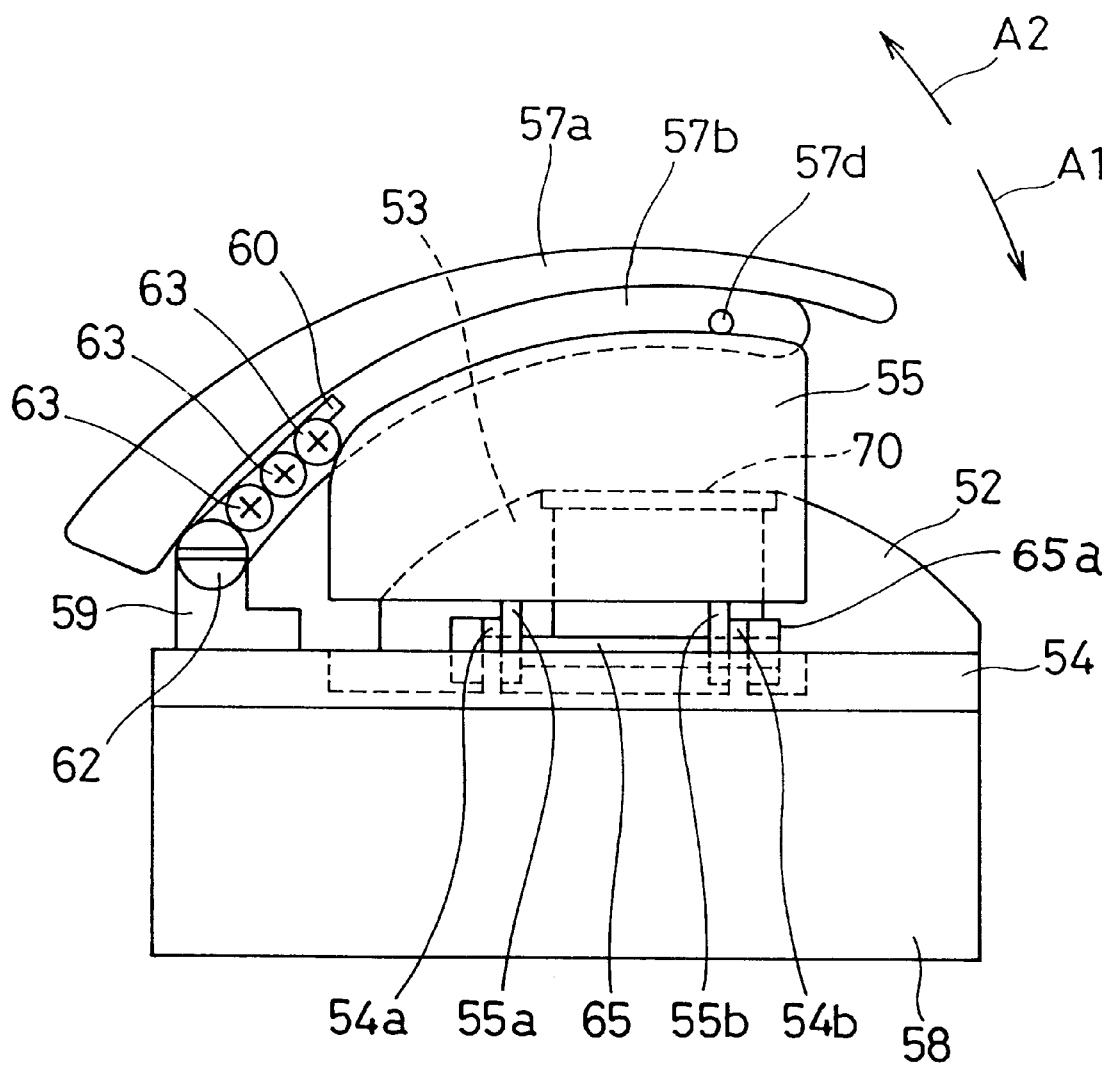
FIG. 6 is a side view of the detecting section of the first embodiment of the present invention.

In these Figures, the base member 51 includes bases 52, 53 for mounting a middle finger F of a human hand (FIGS. 8 and 9) as a portion of the living body to be inspected and a substrate 54 for supporting the bases 52, 53 (FIG. 6). Two sidewall members 55, 56 capable of elastically holding the middle finger F (hereafter referred to as finger F) mounted on the bases 52, 53 from both sides thereof are disposed on the substrate 54 so as to hold the bases 52, 53 therebetween (FIG. 9). Also, a cover member 57 is provided to cover an upper part of the finger F to be mounted on the bases 52, 53 (FIG. 6). Further, the substrate 54 is fixed onto the housing 58 (FIG. 6).

Figure 4:
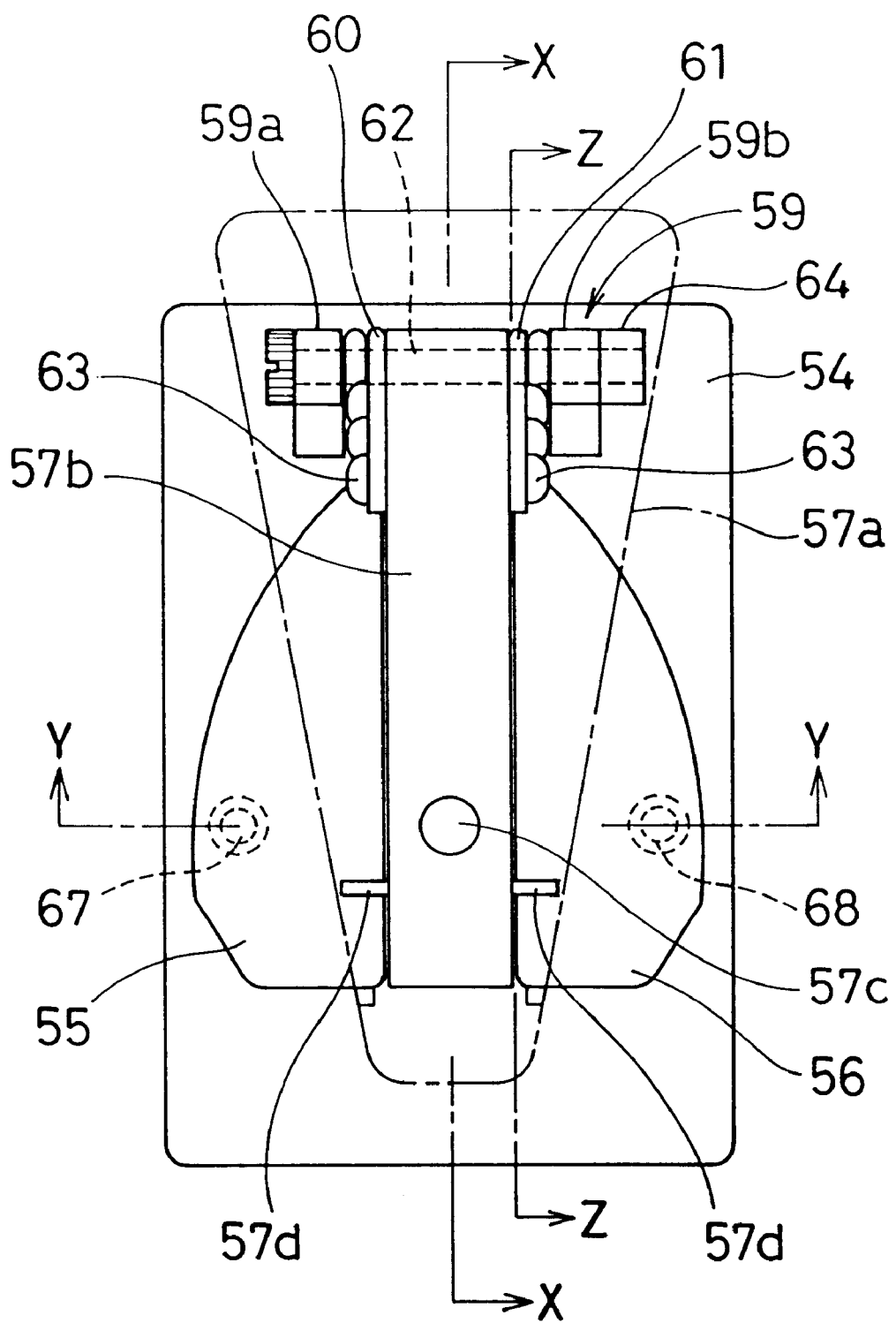
FIG. 4 is a plan view of the detecting section of the first embodiment of the present invention.
Figure 5:
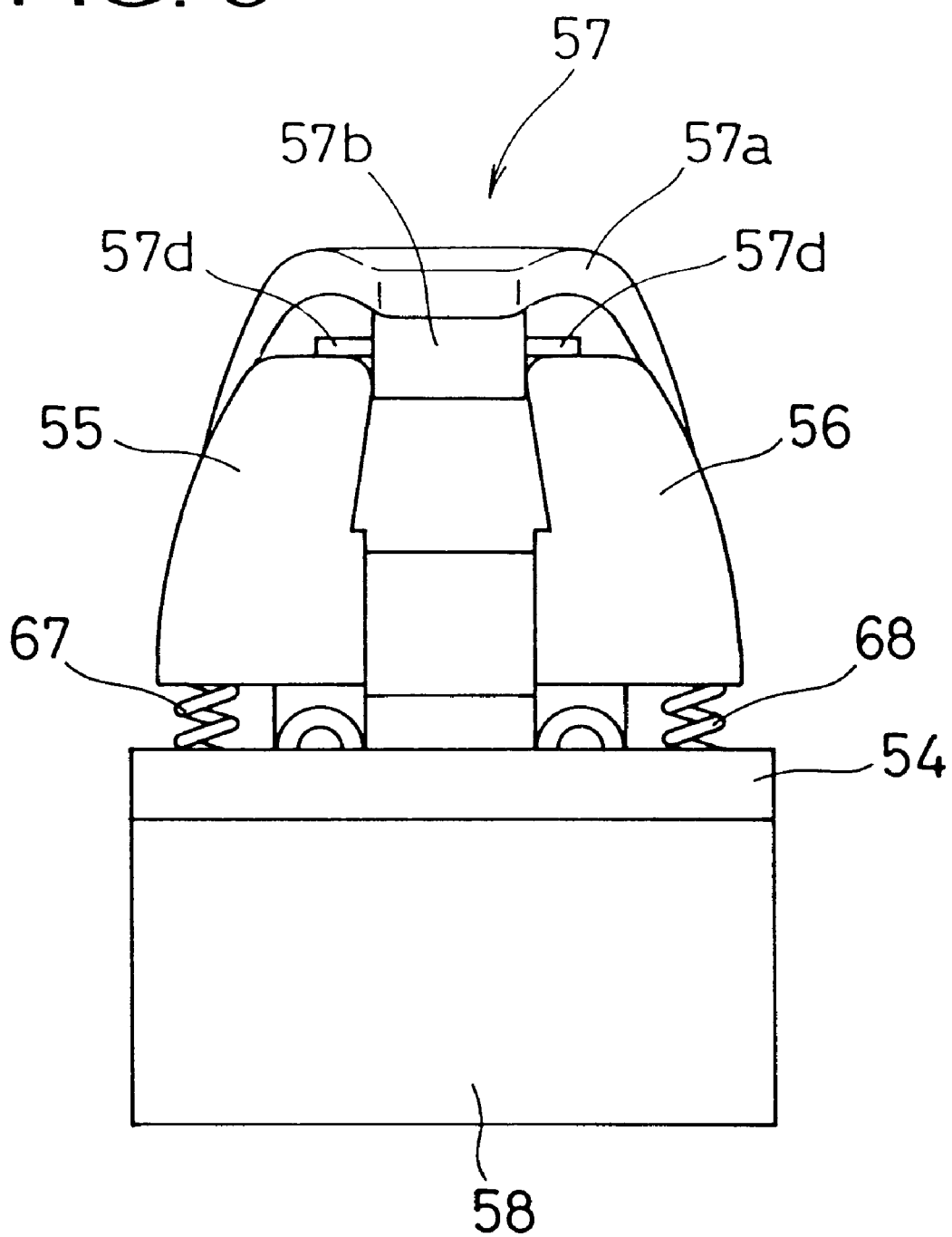
FIG. 5 is a front view of the detecting section of the first embodiment of the present invention.
Figure 11:
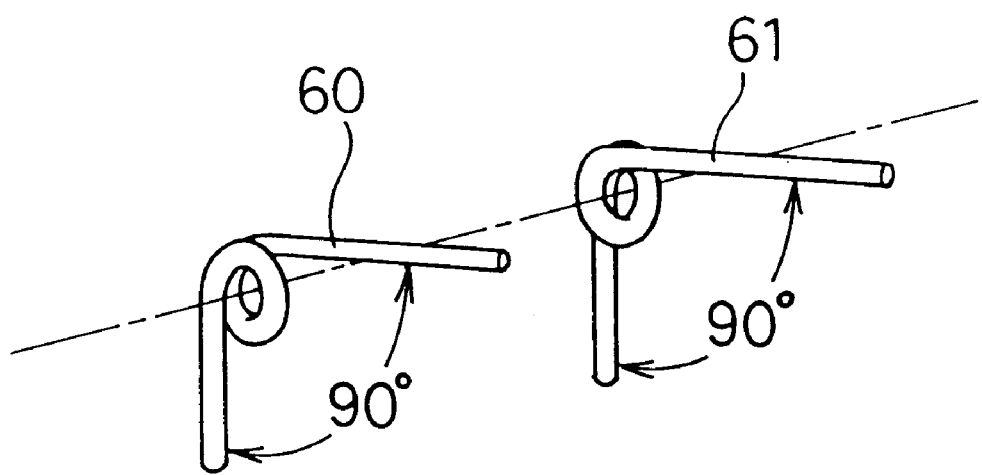
FIG. 11 is a perspective view of a spring used in the detecting section of the first embodiment of the present invention.

The cover member 57 includes a cover 57a and an arm 57b bonded to a lower surface thereof (FIG. 8). As shown in FIG. 4 and FIG. 7, one end of the arm 57b is inserted between the projections 59a and 59b of the arm holder 59 together with springs 60, 61 and is supported by a headed shaft 62 piercing therethrough. The springs 60, 61 are fabricated by allowing a linear member to turn so that the ends thereof form an angle of 90°, as shown in FIG. 11.

With respect to the springs 60, 61 mounted by the shaft 62 between the projections 59a and 59b, one end thereof is fixed to both sides of the arm 57b by three screws 63 and the other end thereof is stopped by engagement with a rear surface of the arm holder 59 as shown in FIGS. 6 and 7. In the state shown in FIG. 6, the ends of the springs 60, 61 form an angle larger than 90° and the springs 60, 61 urge the arm 57b in the direction of the arrow A1. Also, a collar 64 for preventing coming-off is inserted at the tip of the shaft 62.

In other words, the arm 57b and the arm holder 59 form a hinge mechanism, whereby the arm 57b is rotatable in the directions shown by arrows A1 and A2 with the shaft 62 serving as an axis, as shown in FIG. 6, and is urged all the time in the direction shown by an arrow A1 by the urging force of the springs 60, 61.

In the meantime, projections 55a, 55b and 56a, 56b, projecting from the lower surface of the sidewall members 55, 56, are inserted between projections 54a, 54b and 54c, 54d projecting from the substrate 54 and are supported by headed shafts 65, 66 piercing therethrough, as shown in FIGS. 6 and 10. Collars 65a, 66a for preventing the shafts 65, 66 from coming-off are fixed at the tip of the shafts 65, 66.

This allows the sidewall member 55 to rotate in the directions of arrows B1, B2 with the shaft 65 serving as an axis, and allows the sidewall member 56 to rotate in the directions shown by arrows C1, C2 with the shaft 66 serving as an axis, as shown in FIG. 9. Coil springs 67, 68 are mounted between the lower surface of the sidewall member 55 and the upper surface of the substrate 54 and between the lower surface of the sidewall member 56 and the upper surface of the substrate 54, as shown in FIG. 9, and urge the sidewall member 55 in the direction shown by the arrow B1 and the sidewall member 56 in the direction shown by the arrow C1, respectively.

The light source section 11 is mounted in a hole 57c formed in the arm 57b and faces the image capturing section 12 mounted in the housing 58 via a groove 69 between the bases 52 and 53, as shown in FIG. 8.

A glass plate 70 that supports the finger F and transmits the light from the light source section 11 is mounted at an upper opening of the groove 69 so as to extend from the base 52 to the base 53. Two pins 57d shown in FIGS. 4 and 5 project from both sides of the arm 57b and are stopped by engagement with the upper surface of the sidewall members 55 and 56, respectively, when the finger F is not inserted.

Thus, when the finger F is mounted on the bases 52, 53 as shown in FIG. 8, both sides of the finger F are pressed with a light, approximately equal force by the sidewall surface of the sidewall members 55, 56, and the upper surface of the finger F is lightly pressed by the arm 57b, as shown in FIG. 9. This allows the finger F to be positioned on the bases 52, 53.

When the finger F is positioned on the bases 52, 53, the light source section 11 irradiates the finger F, and the transmitted light is received by the image capturing section 12. The image capturing section 12 includes a lens and a CCD, and captures an image of the finger F formed by the transmitted light.

Here, the bases 52, 53 and the glass plate 70 are constructed such that the surface thereof which is brought into contact with the finger F is formed like an arc to be fitted onto a natural curve of the finger F, as shown in FIG. 8. Accordingly, the finger F will not be unnaturally elongated and the blood vessel of the finger will not be in a congested or ischemic state when the finger F is mounted.

Also, the opposing surfaces of the side wall members 55, 56 which are brought into contact with the finger F are not parallel to each other but have a taper (an inclination) such that the upper portions thereof are narrower than the lower portions, as shown in FIG. 9. Accordingly, the sidewall members 55, 56 can give a force component in a downward direction (in a vertical direction), i.e. a force component that presses the finger F onto the bases 52, 53, in addition to a force component in a horizontal direction relative to the finger F. Therefore, it is possible to fix the finger F stably on the bases 52, 53 in a hugging manner.

Figure 18:
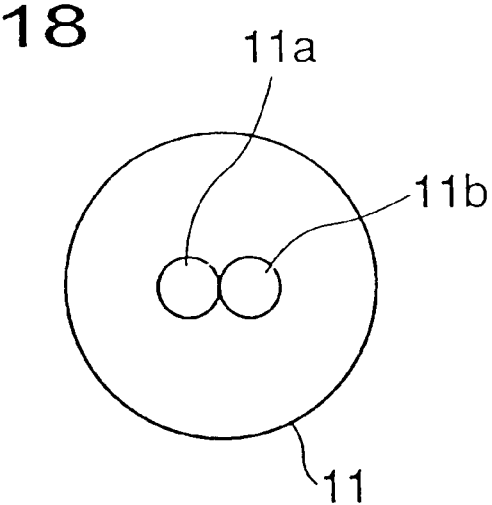
FIG. 18 is a front view of a light source section of the first embodiment of the present invention.

FIG. 18 is a front view of the light source section 11 which includes a light emitting element equipped with a LED 11a and a LED 11b.

L3989 (made by Hamamatsu Photonix Co., Ltd.) having a central wavelength of 830 nm and a half value width of 40 nm is used as the LED 11a, and L2656 (made by the same company) having a central wavelength of 890 nm and a half value width of 50 nm is used as the LED 11b. Further, as mentioned later, only the LED 11a is switched on in "blood vessel width measuring mode".

Hereafter, with reference to the flow charts shown in FIGS. 12 and 13, an explanation will be given with regard to the procedures that are carried out under such a construction for measuring the blood vessel width and the blood component concentration.

(1) Blood vessel width measuring mode

Figure 14:
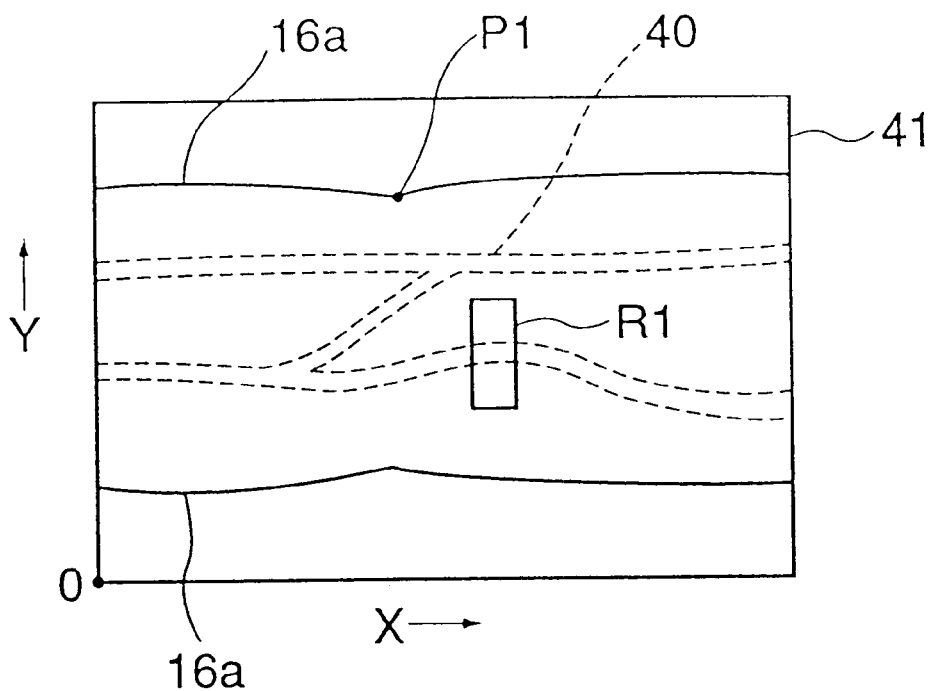
FIG. 14 is an explanatory view showing an example of an image obtained by the first embodiment of the present invention.

First, when a person to be inspected inserts a finger F into the detecting section 1 as shown in FIG. 1 and FIG. 8, an operator operates the inputting section 35 to set the "blood vessel width measuring mode" (step S1), and the finger F is irradiated by the LED 11a (first wavelength) to capture an image. Thereby, an image 41 of a tissue including a blood vessel (vein) image 40 locally present near the skin on the side of the image capturing section 12 is obtained together with a contour 16a of the finger F as shown in FIG. 14 and the image 41 is output to the outputting section 24 as a monitor image (step S2). Next, an analysis region R1 is set in the image 41 (step S3).

Figure 13:
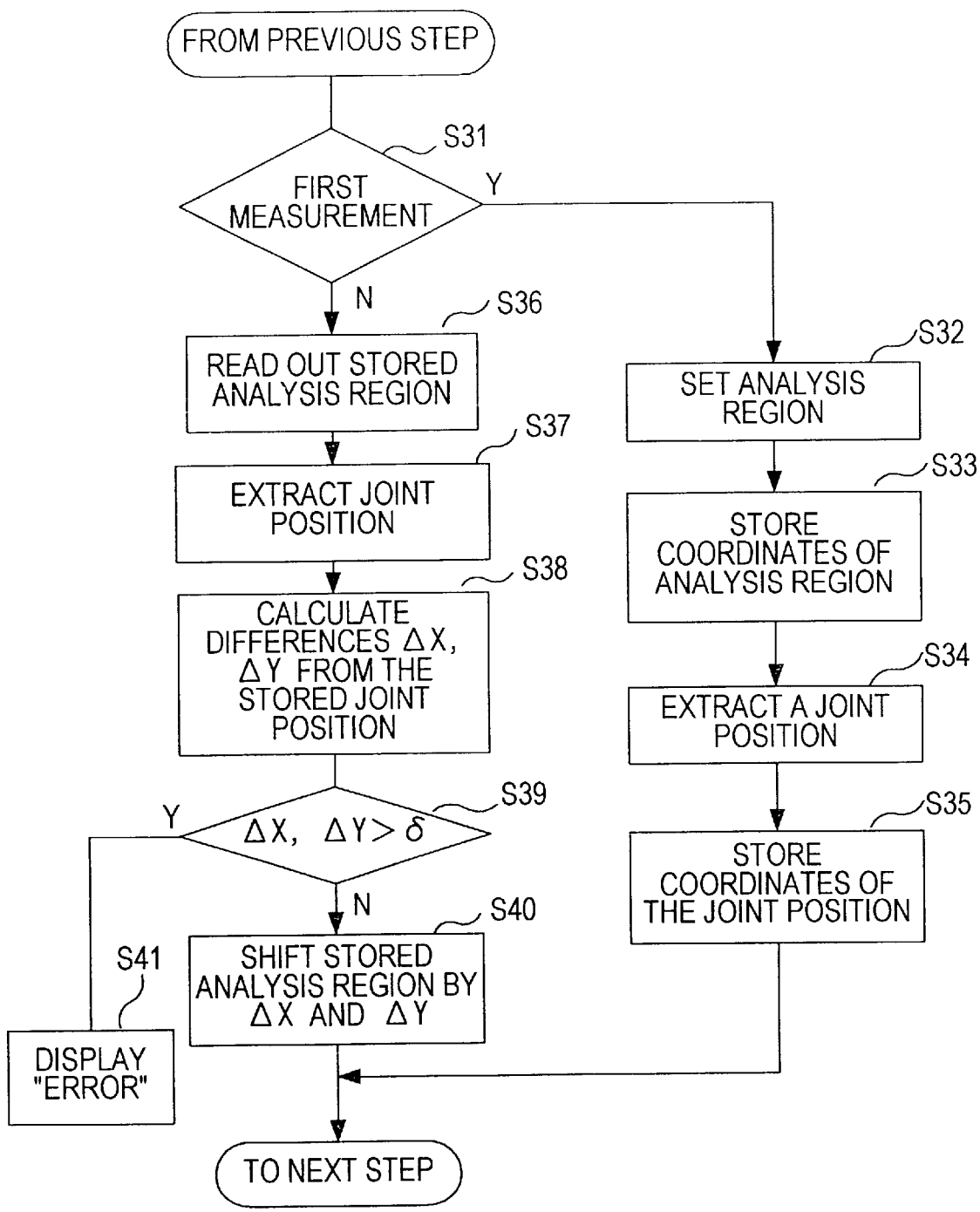
FIG. 13 is a flowchart showing a procedure for determining an analysis region in the first embodiment of the present invention.

The procedure of setting the analysis region R1 is executed by a procedure shown in FIG. 13. That is, when the measurement is carried out for the first time (step S31), an analysis region setting section 34 searches for a region where the blood vessel image 40 has the best contrast and a region determined as a result of the search is set as a rectangular analysis region R1 (step S32). Incidentally, although the analysis region R1 is usually set by the analysis region setting section 34 automatically, a user may set the analysis region R1 manually by operating the inputting section 35 while observing a monitored image output to the outputting section 24.

With respect to the set analysis region R1, coordinates of respective vertices thereof are stored in the storing section 32 with a screen of the image 41 serving as an X-Y coordinate plane (step S33). Next, the feature extracting section 31 extracts a recess position P1 of a joint portion in the contour 16a of the image 41 and allows the coordinates of the extracted position P1 to be stored into the storing section 32 (steps S34, S35).

Figure 15:
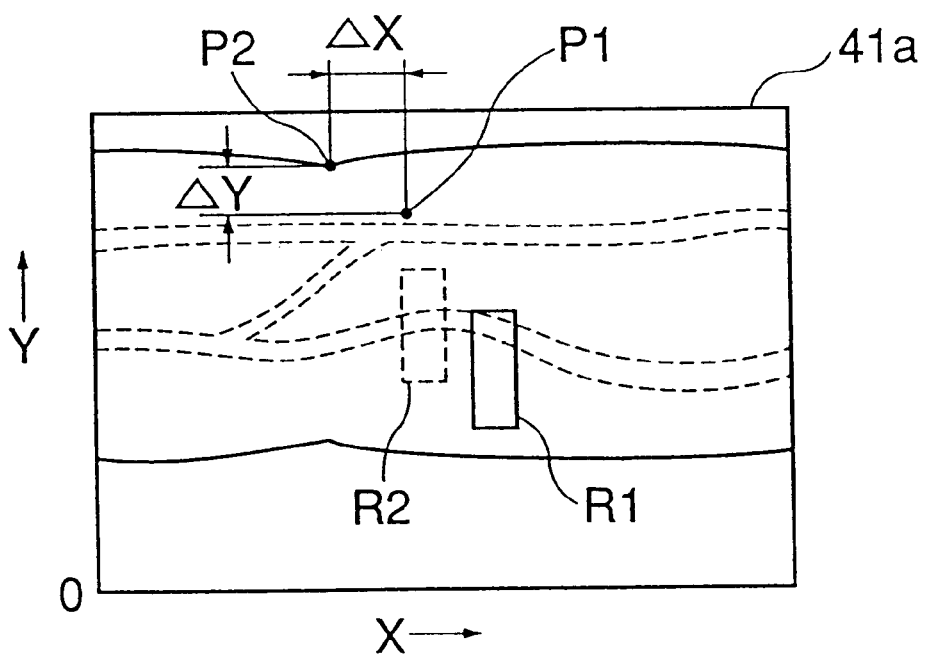
FIG. 15 is an explanatory view showing an example of an image obtained by the first embodiment of the present invention.

Further, when the measurement is carried out for the second time or thereafter in step 31, in the case where, for example, an image 41a shown in FIG. 15 is obtained in the previous step, the stored coordinates of the analysis region R1 are read out and a position P2 of the recess of the joint portion is extracted from the image 41a by the feature extracting section 31 (steps S36, S37).

Next, differences in coordinates Δx, ΔY are calculated by the comparing section 33 with respect to the position P1 which has been set in the measurement at the first time and the position P2 that is extracted at the current time (step S38). Further, when both of Δx, ΔY are within a predetermined allowable range δ (step S39), the analysis region setting section 34 sets a new analysis region R2 by shifting the initially set analysis region R1 by ΔX, ΔY (step S40).

Thereby, the blood vessel site in the region R2 is substantially the same as the blood vessel site in the region R1 which has been set in the measurement at the first time. In this way, even when "n" times of measurement is carried out with respect to a finger or thumb of one person to be inspected time-sequentially (for example, at intervals of 2 hours), the analysis regions R1, R2 . . . Rn are set at respective times and the measurement is carried out always with respect to the same site of the blood vessel. Incidentally, when either of Δx, ΔY exceeds the allowable value δ in step S39, the analyzing section 2 judges that the finger 16 is not correctly placed with respect to the detecting section 1, and "ERROR" is displayed in the outputting section 24.

Figure 12:
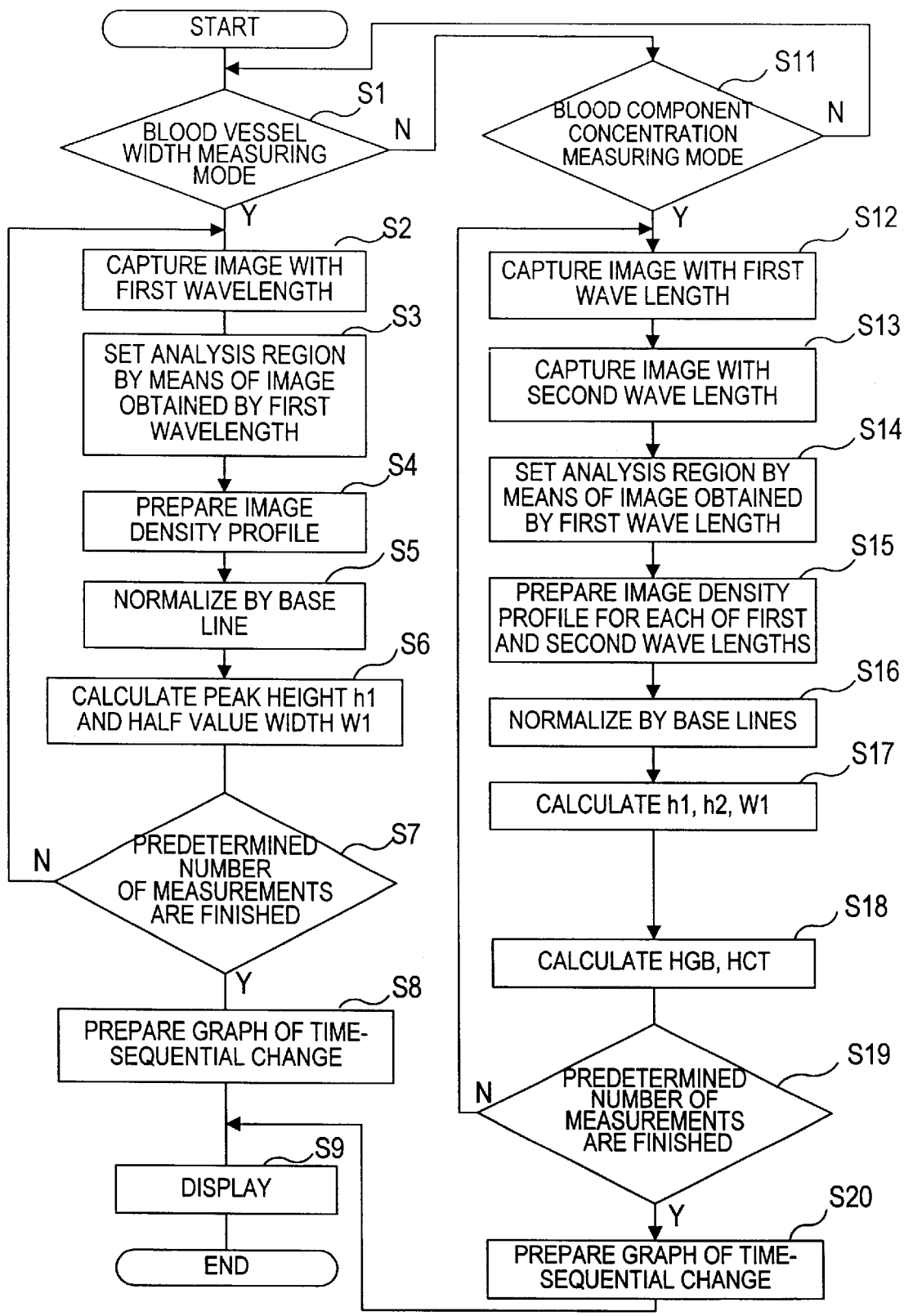
FIG. 12 is a flowchart showing an operation of the detecting section and the analyzing section in the first embodiment of the present invention.
Figure 16:
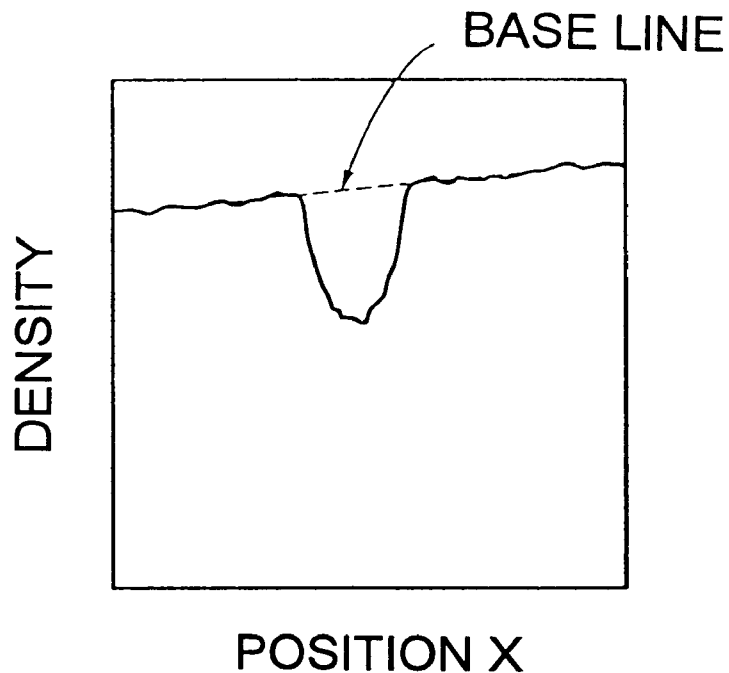
FIG. 16 is an explanatory view showing a concentration profile of an image obtained by the first embodiment of the present invention.
Figure 17:
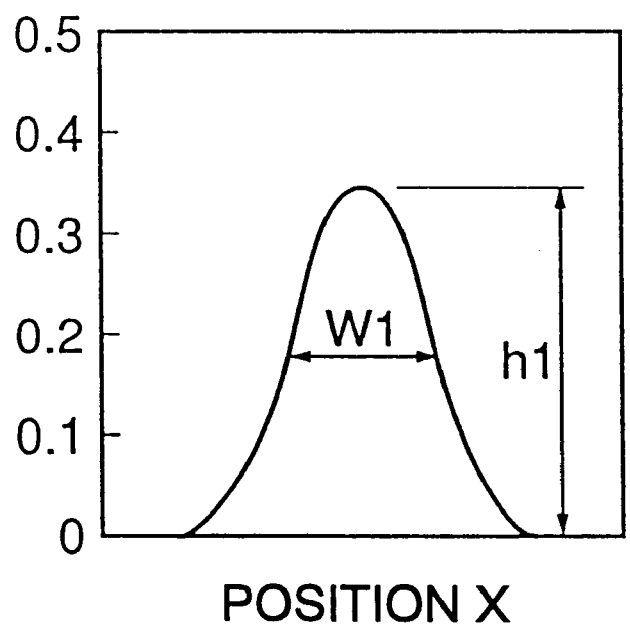
FIG. 17 is an explanatory view showing a normalized concentration profile of the image obtained by the first embodiment of the present invention.

Next, the profile extracting section 21 prepares a density profile (FIG. 16) in a direction perpendicular to the blood vessel in the set analysis region R1 in step S4 of FIG. 12. The quantitating section 22 normalizes the density profile by a base line. The base line is calculated by the least square method or the like from a portion of a density profile other than the blood vessel portion, and the profile of FIG. 16 is normalized by the base line as shown in FIG. 17 (step S5). In this way, the density profile which is not dependent on an amount of incident light can be obtained.

The calculating section 23 calculates a peak height h1 from the normalized density profile (FIG. 17) and calculates a distribution width (half value width) w1 at (½)h1 as the blood vessel width and stores it in the storing section 25 (step S6). Further, when a predetermined number of times of the measurement have been finished, a graph or a table representing a time-sequential change of the calculated blood vessel width is prepared and displayed (steps S7 through S9).

Figure 19:
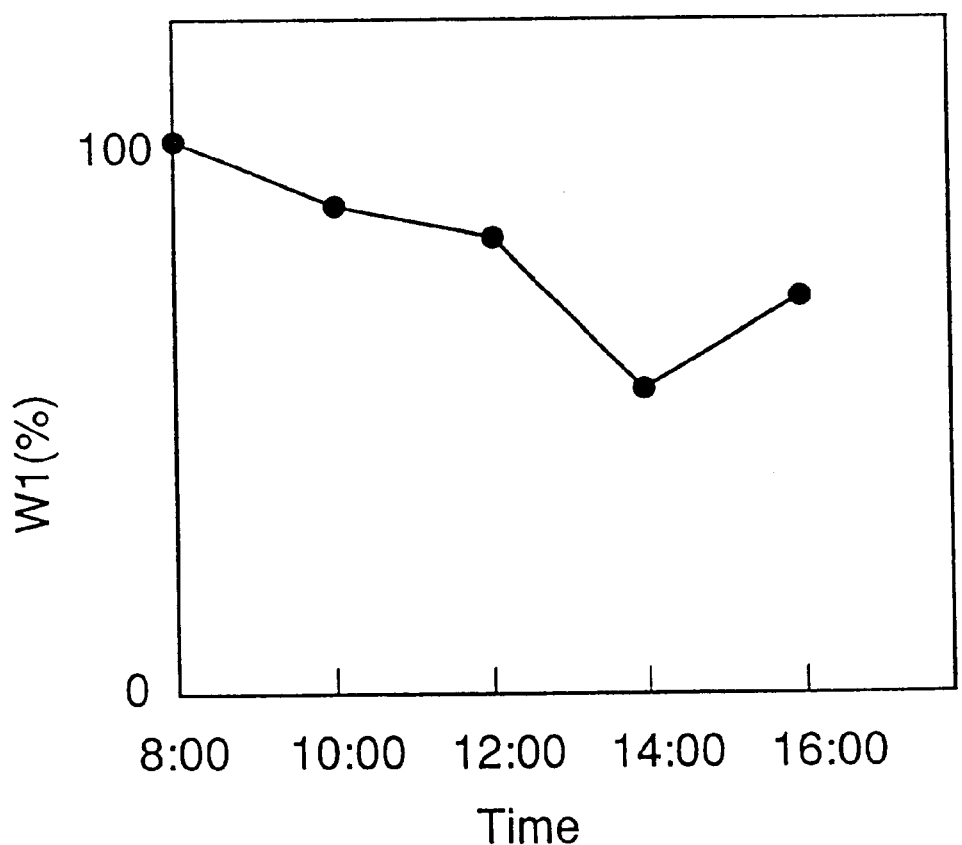
FIG. 19 is an explanatory view showing a display example displayed by the first embodiment of the present invention.

FIG. 19 shows an example of displaying a relative time-sequential change of the blood vessel width w1 in a graph by the outputting section 24 when the measurement is carried out at intervals of two hours with respect to a finger or thumb of one person to be inspected.

(2) Blood component concentration measuring mode

First, the operator operates the inputting section 35 (FIG. 1) to set a "blood component concentration measuring mode" as shown in FIG. 12 (step S11). The finger F of the person to be inspected is irradiated successively by LED 11a (first wavelength) and LED 11b (second wavelength) and images are respectively captured (steps S12, S13). An analysis region is set with respect to the image captured by the first wavelength by the same procedure as that in step S3, that is, the procedure shown in FIG. 13 (step S14).

Next, the profile extracting section 21 prepares a density profile (FIG. 16) for each of the images obtained by the first wavelength and the second wavelength, (step S15). The quantitating section 22 normalizes each of the density profiles by a base line as shown in FIG. 17 (step S16).

Then, the calculating section 23 calculates peak heights h1, h2 and a half value width w1 of each of the normalized density profiles (step S17), and calculates a hemoglobin concentration HGB and a hematocrit HCT in the following way (step S18).

That is, when the scattering coefficient of blood at a first wavelength is designated by S1, the light absorption coefficient thereof is designated by A1, and Beer's Law approximately holds, then $$\log(1-h1) = -k(S1+A1)w1 \quad (1)$$

where k designates a proportional constant.

Meanwhile, the scattering coefficient S1 and the light absorption coefficient A1 can be considered as being proportional respectively to the hematocrit HCT and the hemoglobin amount of blood.

$$S1 = \sigma1 \cdot HCT,\ A1 = \sigma2 \cdot HGB \quad (2)$$

Accordingly, $$\log(1-h1) = -(k\sigma1 \cdot HCT + k\sigma2 \cdot HGB) \cdot w1 \quad (3).$$

Then, also with respect to the peak height h2 obtained from the image by LED 11b (second wavelength), $$\log(1-h2) = -k(S2+A2) \cdot w1 = -(k\sigma3 \cdot HCT + k\sigma4 \cdot HGB) \cdot w1 \quad (4)$$

Since k, σ1, σ2, σ3 and σ4 are experimentally determined, HGB and HCT are obtained by h1, h2, and w1.

However, in actual cases, the image is blurred by a tissue present from the blood vessel to the epiderm and accordingly, the observed peak value is reduced compared with that in the case where the tissue is not present. Accordingly, $$\log(1-h1) = -k(S+A)w1 + T \quad (5)$$

where S designates the scattering coefficient of blood, A designates the absorption coefficient of blood and T designates a term representing influence by the living body tissue.

Now, it has been experimentally found that T is made to be comparatively constant by selecting, as the analysis region, a portion where the contrast of the blood vessel image is maximized among the obtained images. Accordingly, even if experimentally determined T is used, it poses no practical problem.

Calculated HGB and HCT are stored into the storing section 25. When such a measurement is repeated by a predetermined number of times, the calculating section 23 prepares a graph or a table representing a time-sequential change of the calculated values and displays it (steps S19, S20)

Figure 20:
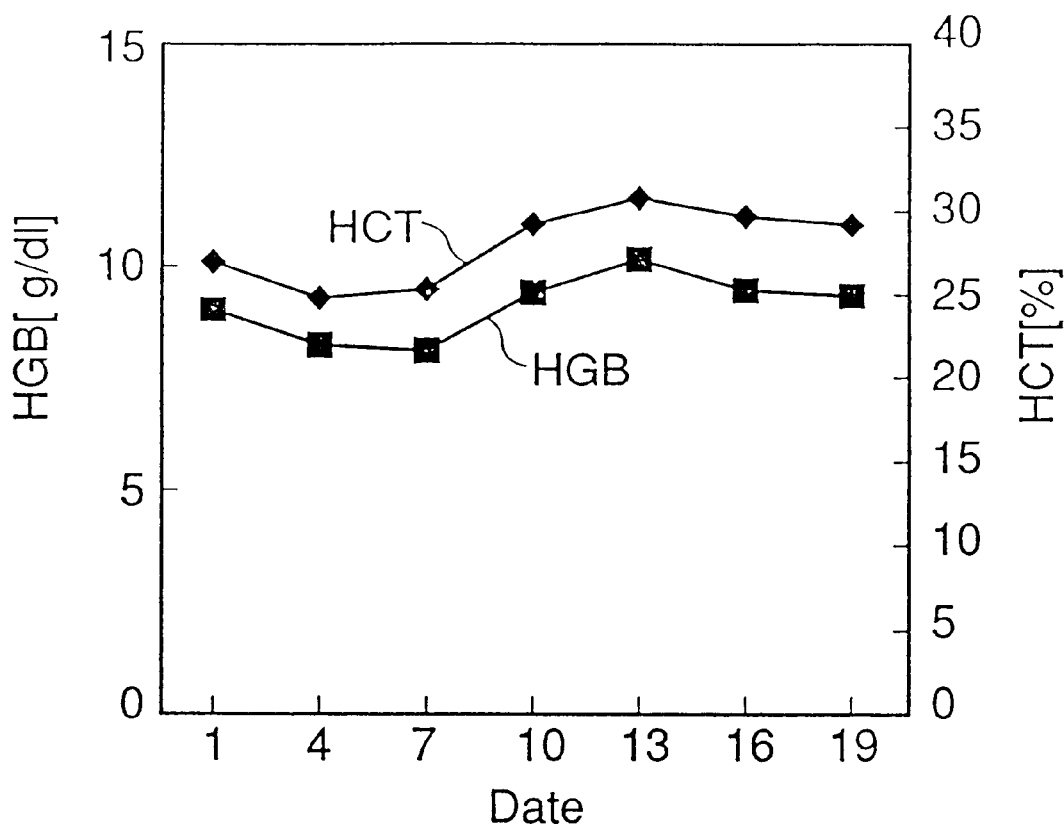
FIG. 20 is an explanatory view showing another display example displayed by the first embodiment of the present invention.

FIG. 20 shows an example in which the measurement has been carried out at intervals of two days with respect to a finger or thumb of a person to be inspected and time-sequential changes of HGB and HCT are displayed by the outputting section 24 in graphs.

SECOND EMBODIMENT

Figure 21:
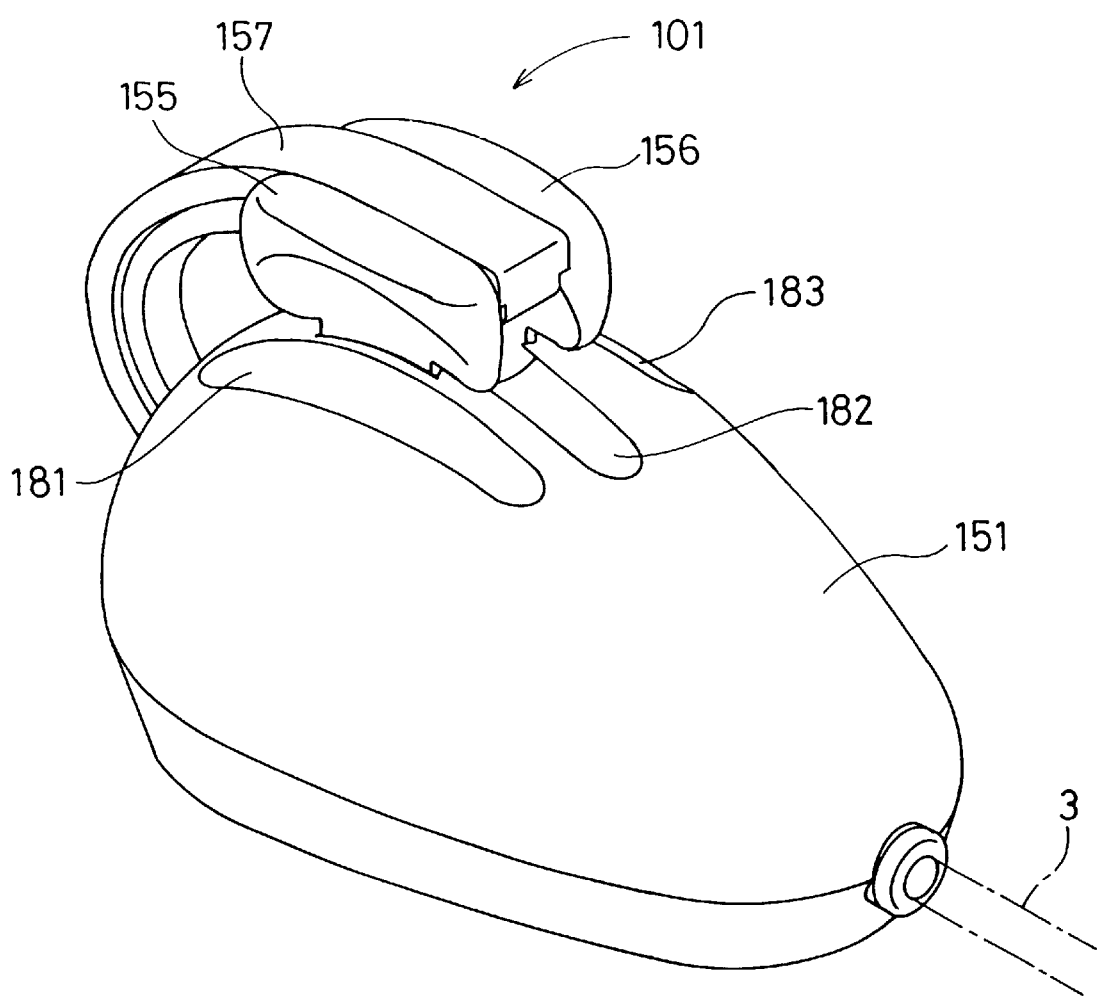
FIG. 21 is a perspective view showing a detecting section of a second embodiment of the present invention.
Figure 22:
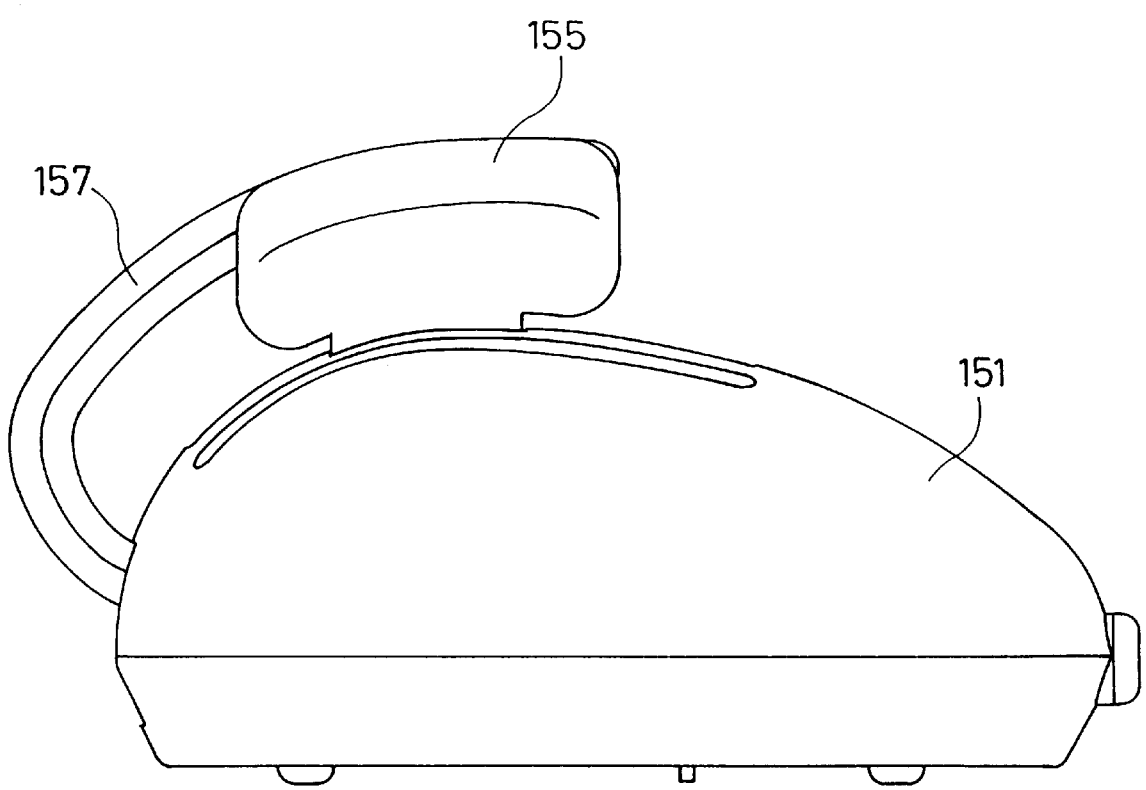
FIG. 22 is a side view showing the detecting section of the second embodiment of the present invention.

FIG. 21 is a perspective view showing a detecting section 101 according to a second embodiment of the present invention. In this embodiment, the construction of the detecting section 1 of the first embodiment has been modified and the other constructions are substantially the same as in the first embodiment.

FIGS. 22 to 27 are a left side view, a plan view, a front view, a rear view, a bottom view, and a longitudinal cross-sectional view, respectively showing the detecting section 101. Here, a right side view is symmetrical to the left side view, so that the right side view is not shown here.

Figure 28:
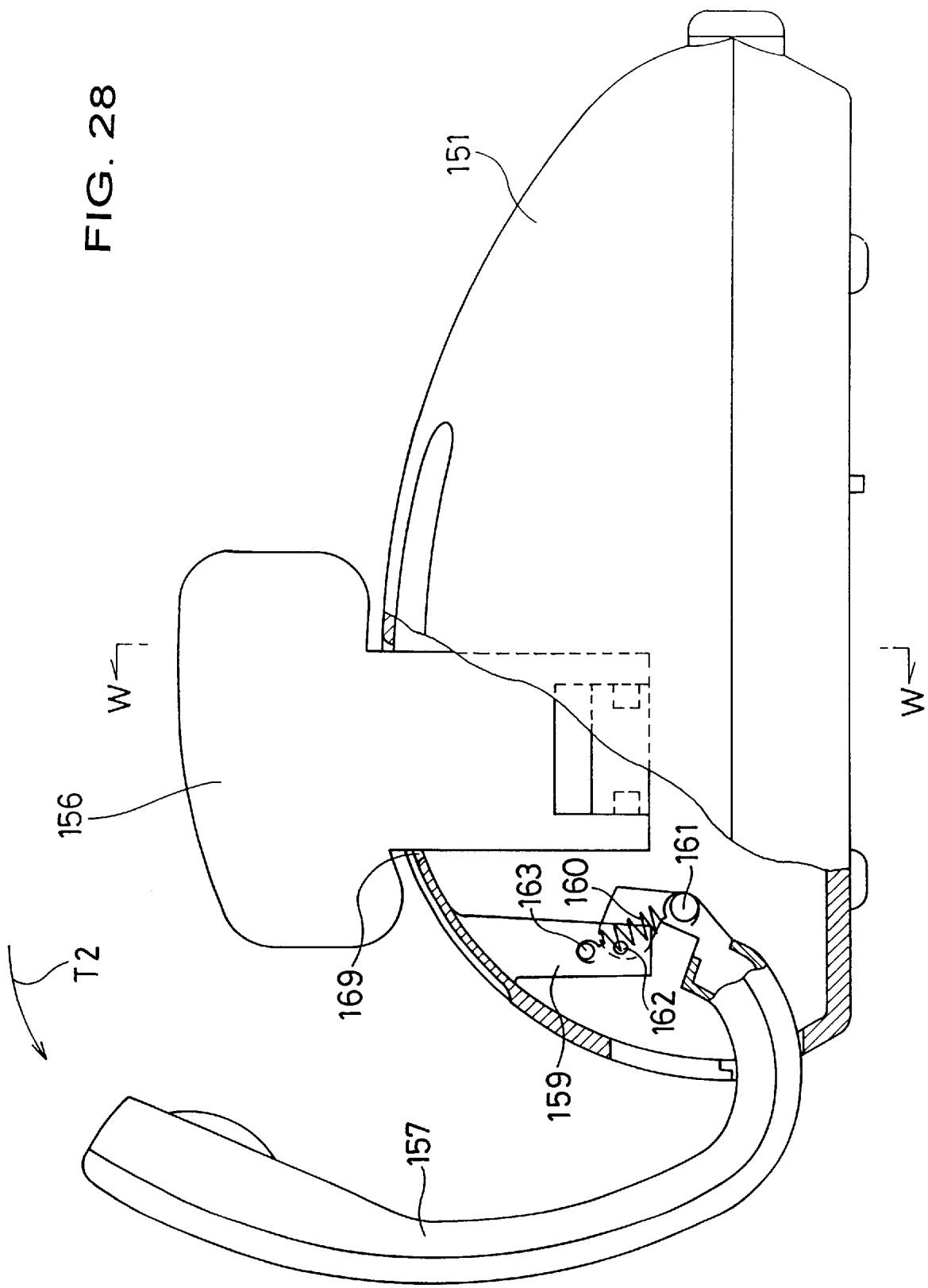
FIG. 28 is a side view showing the detecting section of the second embodiment of the present invention with an essential portion exposed.
Figure 29:
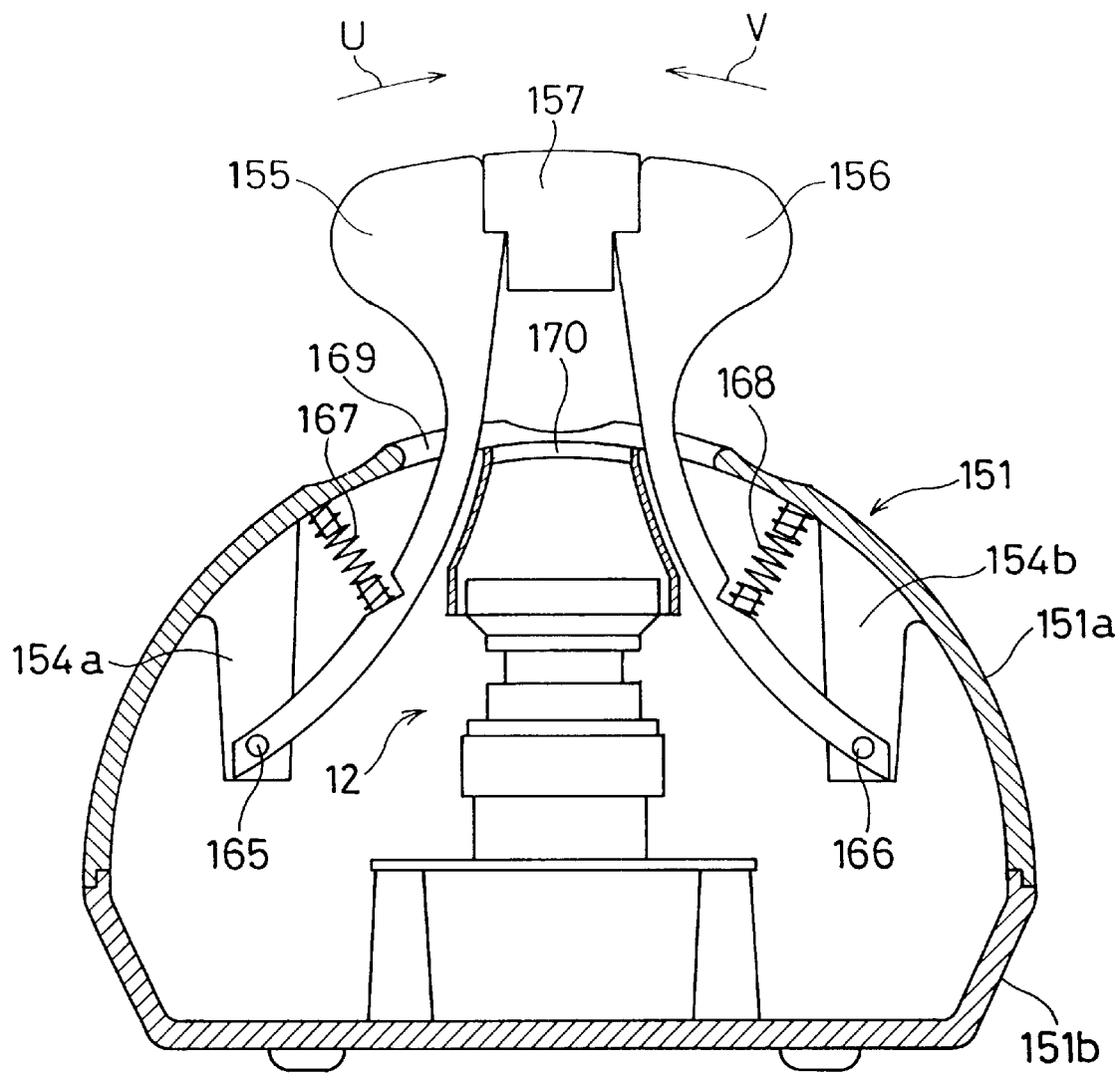
FIG. 29 is a cross-sectional view of FIG. 28 as viewed in the direction of the arrows along the line W—W.
Figure 30:
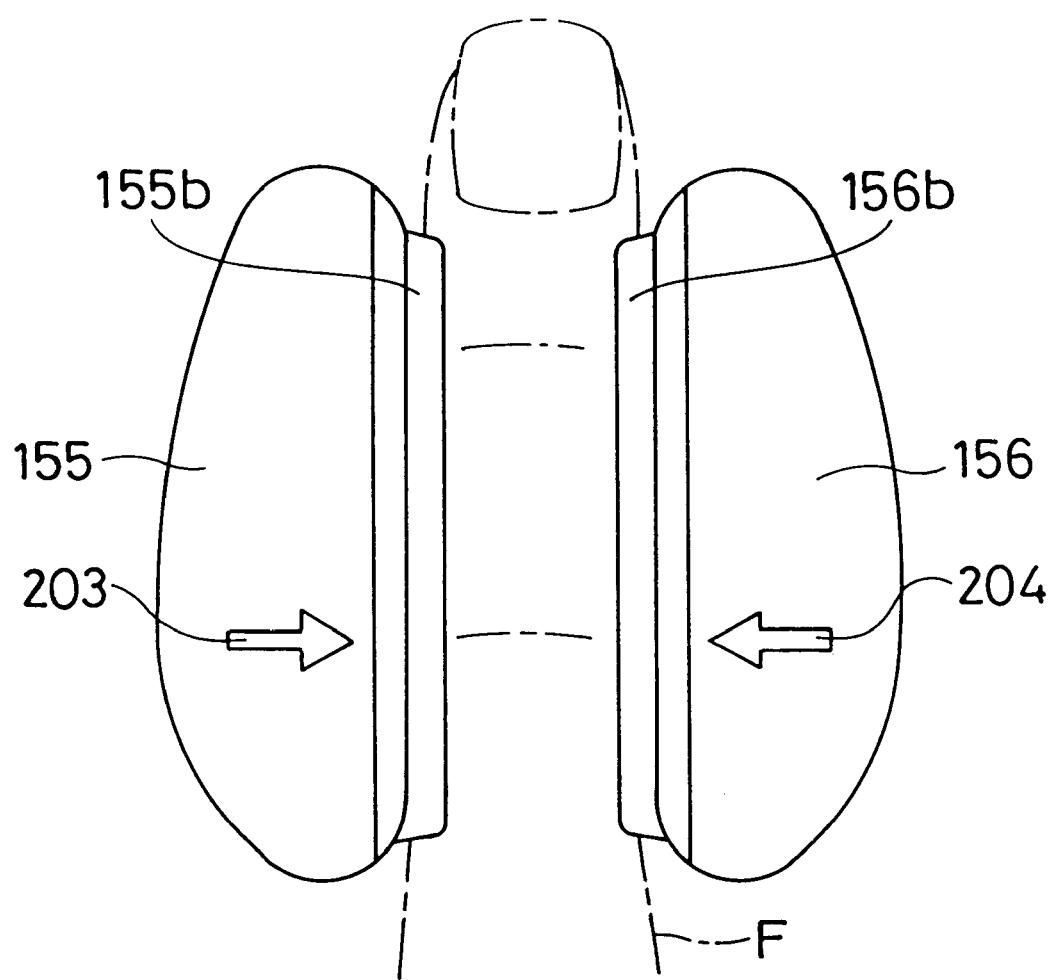
FIG. 30 is an explanatory view showing an operation of the detecting section of the second embodiment of the present invention.
Figure 31:
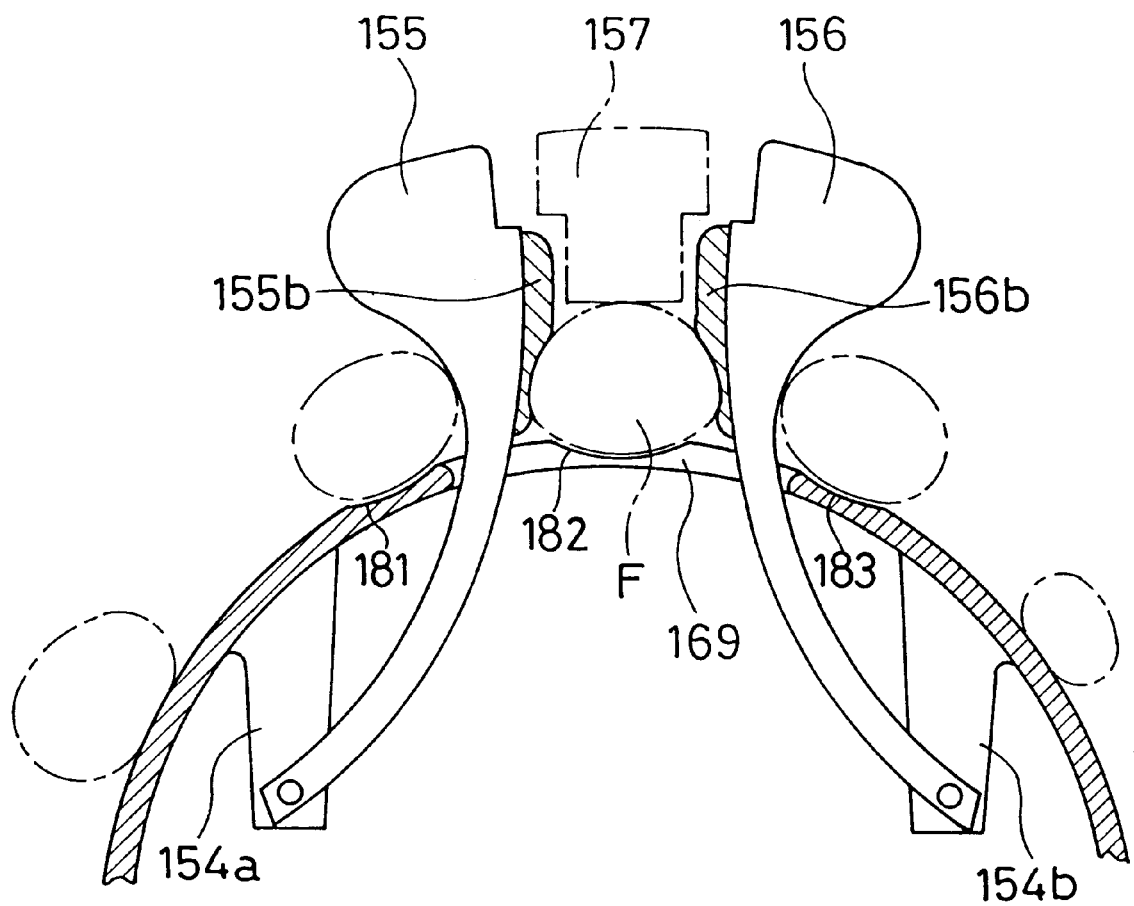
FIG. 31 is an explanatory view showing the operation of the detecting section of the second embodiment of the present invention.

FIG. 28 is a side view showing the detecting section 101 with an essential portion exposed. FIG. 29 is a crosssectional view taken along the line W—W of FIG. 28. FIGS. 30 and 31 are explanatory views showing an operation of the essential portion.

This embodiment is designed such that the whole hand (the palm, the thumb, and the fingers of the hand) can be stably mounted and measured without strain in a natural state and the person to be inspected does not feel a fatigue at the time of mounting.

In other words, the base member 51 and the housing 58 shown in FIG. 3 of the first embodiment are integrated into one as shown in FIG. 21 to form a hollow, oval-shaped housing 151, and a top portion of the upper surface of the housing 151 is allowed to function as the bases 52, 53 of the first embodiment.

At the time of measurement, as in FIG. 8 of the first embodiment, the middle finger F is inserted between the two side wall members 155 and 156; the other fingers and the thumb are symmetrically disposed two by two on the outside of the sidewall members 155 and 156; and the middle finger F is pressed by the arm 157 (See FIG. 30 and FIG. 31). At this time, by mounting the whole palm of the hand on the housing 151, the oval convex curved surface thereof conforms well to a concave curved surface formed by the palm of the hand and the fingers and the thumb thereof in a natural state.

As shown in FIG. 29, the housing 151 is made of an upper housing 151a and a bottom portion 151b, and the two are integrally joined by mutual engagement of their peripheral portions. The lower portions of the sidewall members 155, 156 are pivotally supported by shafts 165, 166 onto the projections 154a, 154b projecting downward from the inside of the upper housing 151a in the housing 151 and are urged respectively in the directions of arrows U, V by springs 167, 168. In other words, the projections 154a, 154b and the shafts 165, 166 constitute a hinge mechanism that supports the sidewall members 155, 156 to be rotatable in the directions of the arrows U, V. The upper portions of the sidewall members 155, 156 protrude to outside from an opening 169 provided at the upper central portion of the housing 151.

> The finger F, which is a part of the living body, is disposed between the two sidewall members 155, 156 and are elastically held from both sides (FIG. 31). Although the finger F, as an object of measurement, is assumed to be a middle finger here, the other fingers or the thumb may also be measured.

In this embodiment, in order to place the middle finger F between the sidewall members 155, 156 and to mount the other fingers and the thumb two by two on the outside of the respective sidewall members 155, 156, recesses 181, 182, 183 (FIG. 23 and FIG. 31) that conform to the shape of the respective fingers and thumb are provided so that the index finger, the ring finger, and the like can be suitably mounted on the surface of the housing 151, whereby the fingers and the thumb are each allowed to be fitted well onto the surface of the housing 151.

Also, the outside wall portions of the sidewall members 155, 156 have recessed concave portions 155a, 156a near the surface of the housing 151 (FIG. 24), and the concave portions 155a, 156a form a curved surface that fits onto a respective curved surface on the middle finger side of the index finger and the ring finger which are on both sides of the middle finger. Also, since the thickness of the sidewall members 155, 156 at the finger-mounting portion is smaller, measurement can be performed by mounting the palm, the fingers, and the thumb of the hand in a natural state without greatly widening the fingers.

Further, in order to heighten the sense of fitness, the inside wall portions of the sidewall members 155, 156 may be designed as shown, for example, in FIG. 30 and FIG. 31.

FIG. 30 and FIG. 31 are views of the sidewall members 155, 156 as viewed from the above and from the front, respectively. In this case, the inside wall portions of the sidewall members 155, 156 are provided with non-light-transmitting, soft elastic bodies 155b, 156b (preferably black) made of rubber or sponge. Accordingly, the sidewall members 155, 156 can stably hold the middle finger F therebetween without strain and in conformity with its shape.

Also, an effect of obtaining better optical information is produced because the light radiated from the light source section 111 (FIG. 27) does not leak out to the image capturing section 12 side from a gap formed between the sidewall members 155, 156 and the finger F.

Figure 27:
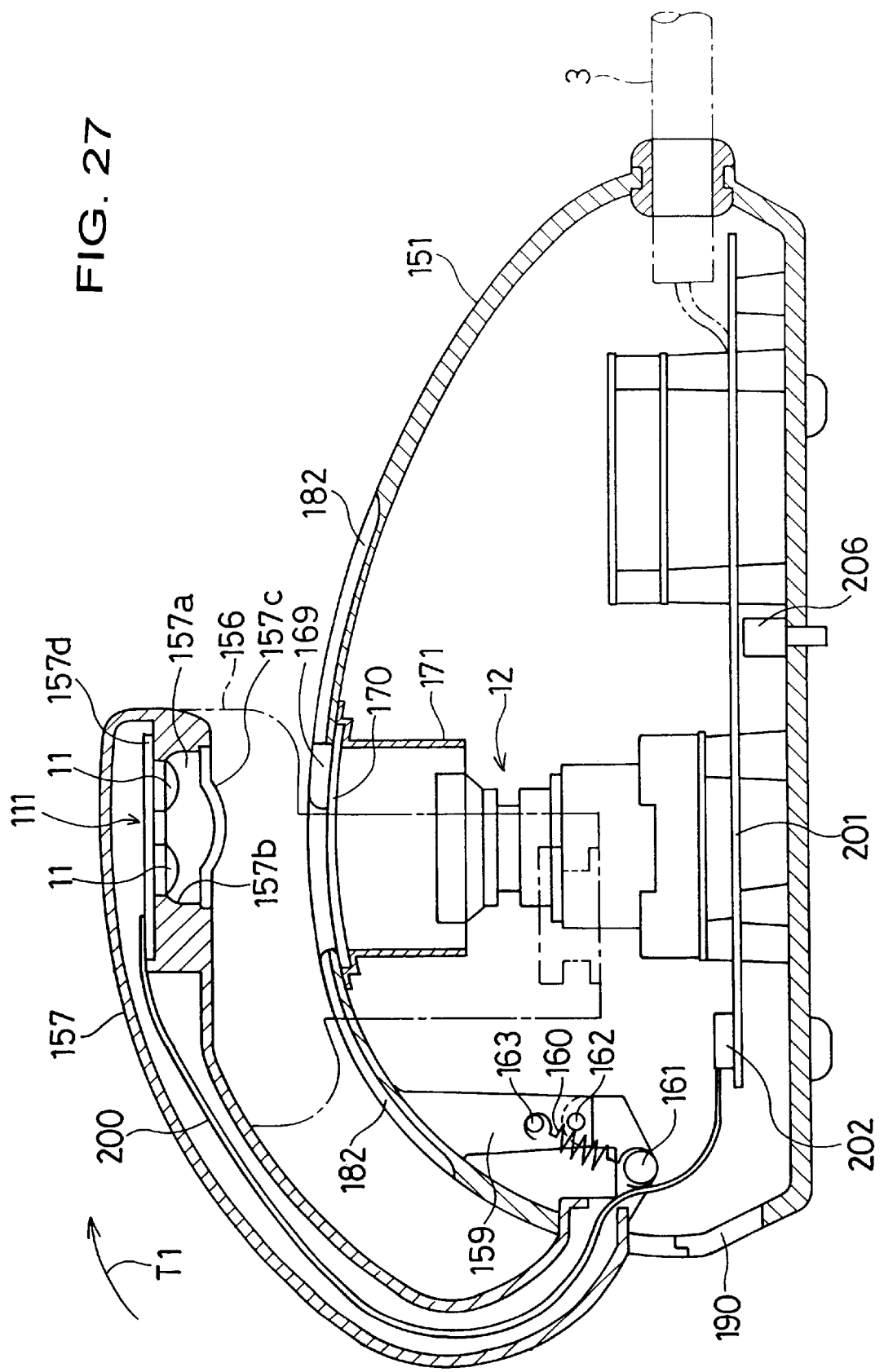
FIG. 27 is a longitudinal cross-sectional view showing the detecting section of the second embodiment of the present invention.

As shown in FIG. 27, the arm 157 is rotatably supported at its one end with a shaft 162 by a projection 159 projecting downwards from the inside surface of the upper housing 151a in the housing 151, and protrudes from an opening 190.

The arm 157 is supported by a toggle mechanism such that it tends to rotate in the direction of approaching the sidewall members 155, 156, namely, in the direction of arrow T1, when the other end is at a position near the sidewall members 155, 156 as shown in FIG. 27, and it tends to rotate in the direction away from the sidewall members 155, 156, namely, in the direction of arrow T2, when the other end is at a position distant from the sidewall members 155, 156 as shown in FIG. 28.

In this toggle mechanism, bosses 161 and 163 are disposed on the end of the arm 157 and on the projection 159, respectively, and a spring 160 is hooked and extends therebetween, as shown in FIG. 27. The distance between the bosses 161, 163 changes by rotation of the arm 157 in a direction of arrow T1 or T2. The state in which the arm 157 is in contact with the sidewall members 155, 156 as shown in FIG. 27 is referred to as an initial position. When the arm 157 is rotated in the direction shown by arrow T2, the distance between the bosses 161, 163 increases, so that the spring 160 acts to shorten the distance between the bosses. In other words, the arm 157 acts to return to the side of the sidewall members 155, 156.

When the boss 161, the shaft 162, and the boss 163 are aligned by further rotation of the arm 157 in the direction shown by arrow T2, the distance between the bosses begins to decrease, so that the arm 157 in turn acts to rotate in the direction away from the sidewall members 155, 156. Then, it stops rotating when the back of the arm 157 comes in contact with the edge of the housing opening 190. By this, the person to be inspected no longer needs, in inserting the middle finger of one hand between the sidewall members 155, 156, to open and hold the arm 157 using the other hand, whereby the operability is improved.

In this embodiment, a light source section 111 for irradiating the finger F is disposed at the other end of the arm 157 in the same manner as the light source section 11 of the first embodiment; an image capturing section 12, similar to the image capturing section 12 of the first embodiment, is disposed inside the housing 151; and further a light-transmitting plate 170 made of acrylic resin corresponding to the glass plate 70 of the first embodiment is disposed at the opening 169 of the housing 151, as shown in FIG. 27. Here, the numeral 171 denotes a hood that connects the light-transmitting plate 170 and the image capturing section 12.

In the light source section 111, two light emitting elements 11 shown in FIG. 18 and used for the light source section of the first embodiment are mounted on the substrate 157a to increase the amount of light, and the substrate 157d is mounted at an upper portion of the opening 157a at the other end of the arm 157 so that the light emitting elements 11 face downwards. Further, the opening 157a has a wall surface 157d that widens like a cone in a downward direction, and a white or silver coating is formed on the wall surface, so that the light from the two light emitting elements 11 is effectively reflected towards the image capturing section 12.

Also, in applying a light to the finger F, there are cases in which a sufficient light cannot be supplied to the inside of the living body because the light is randomly reflected due to fine unevenness of the skin surface. Accordingly, in this embodiment, in order to increase the efficiency of light incidence into the finger F, a light transmitting member 157c that is brought into contact with the finger F is disposed in the opening 157a at the light emitting portion, whereby the light is applied after eliminating the unevenness of the skin surface. This allows the light to be efficiently supplied into the finger F, so that good optical information can be obtained at the image capturing section 12. Here, it will be effective if the light transmitting member 157c has a shape that is convex in the downward direction, namely, a shape that is convex toward the finger F side, as shown in FIG. 27.

Also, the arm 157 is designed to be hollow as shown in FIG. 27; a lead wire 200 is disposed in the arm 157; and supply of electric power to the light source section 111 is conducted from an analyzing section (personal computer) 2 (FIG. 2) through a cable 3, a substrate 201, a connector 202 and the lead wire 200. Accordingly, the lead wire 200 can be separated from the substrate 201 at the connector 202. This construction allows separation of the detecting section 101 of this embodiment into an upper housing 151a side and a lower housing 151b side, so that the assemblage at the time of manufacture and the check of the inside at the time of maintenance are facilitated.

Figure 23:
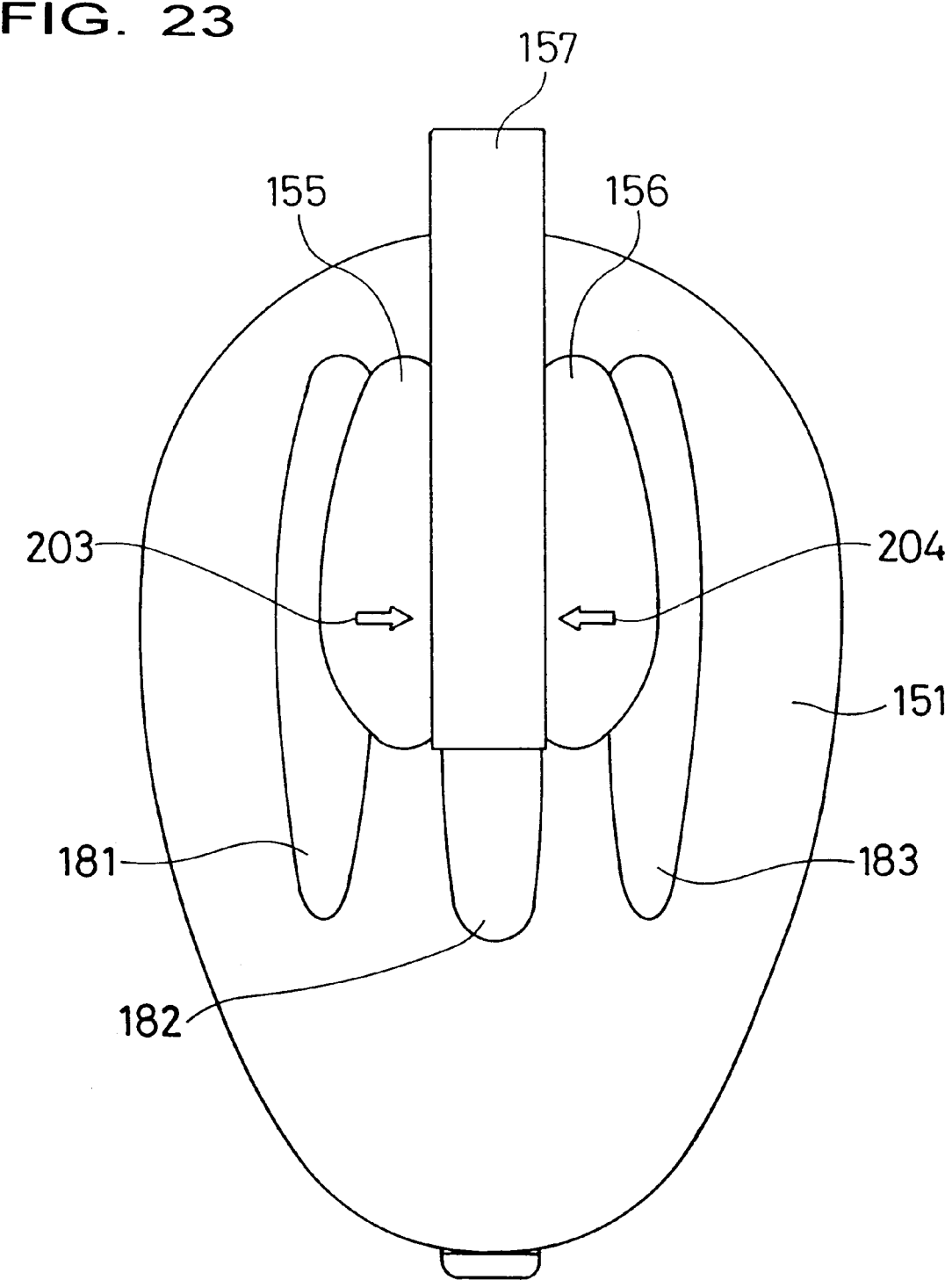
FIG. 23 is a plan view showing the detecting section of the second embodiment of the present invention.
Figure 24:
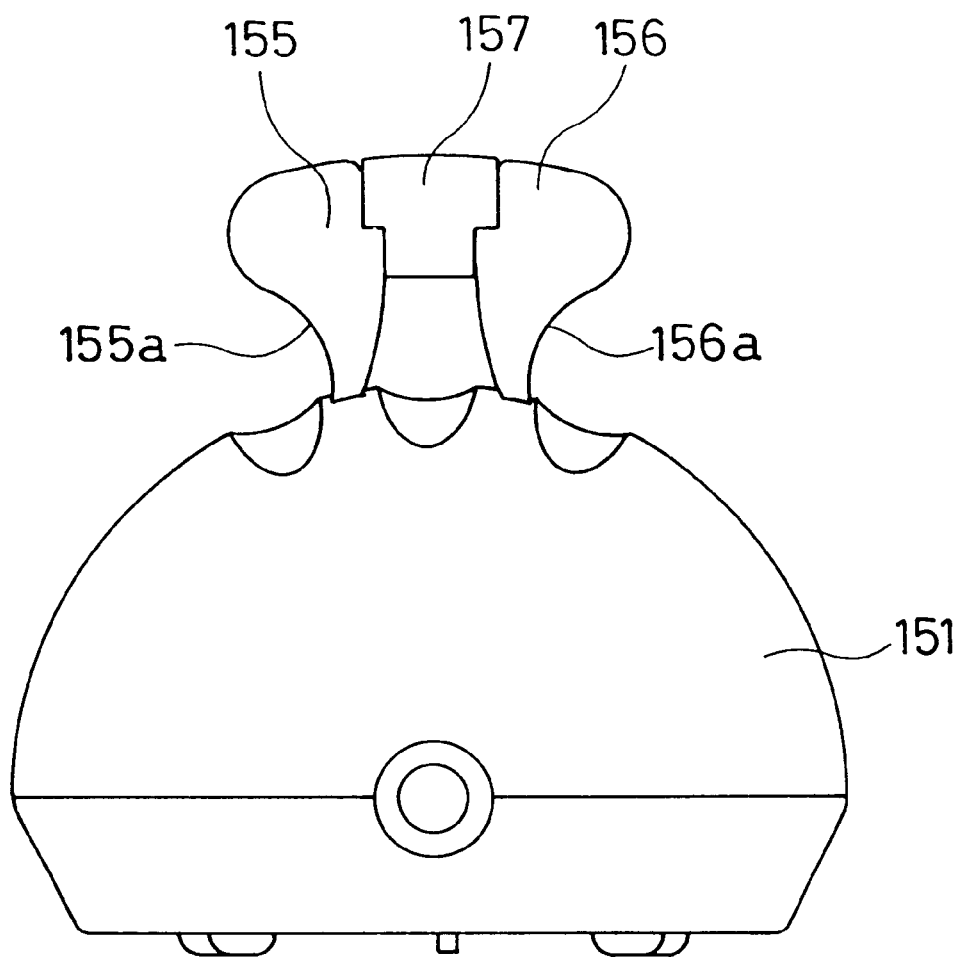
FIG. 24 is a front view showing the detecting section of the second embodiment of the present invention.
Figure 25:
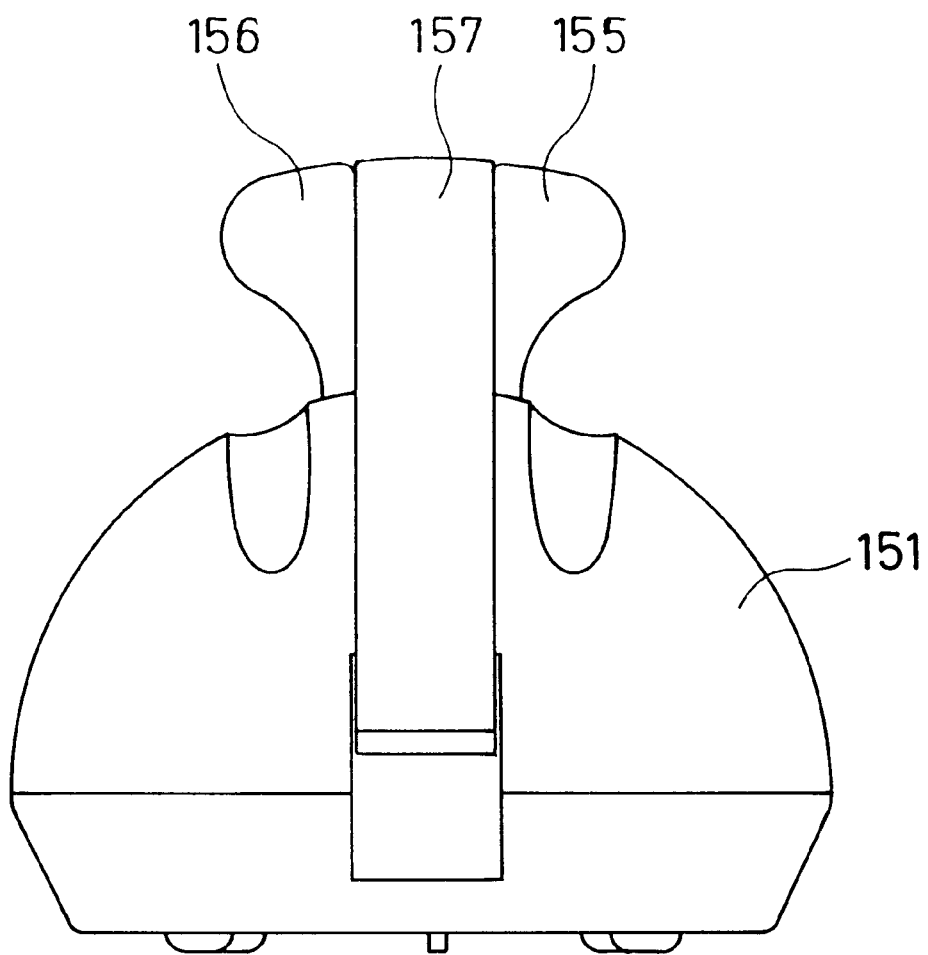
FIG. 25 is a rear view showing the detecting section of the second embodiment of the present invention.

As shown in FIG. 23, positioning marks 203, 204 are provided on the upper surface of the sidewall members 155, 156. These are for positioning the finger F in a longitudinal direction when the finger F is inserted between the sidewall members 155, 156 at the time of measurement. A second joint of the finger F, for example, is positioned at the marks.

Figure 26:
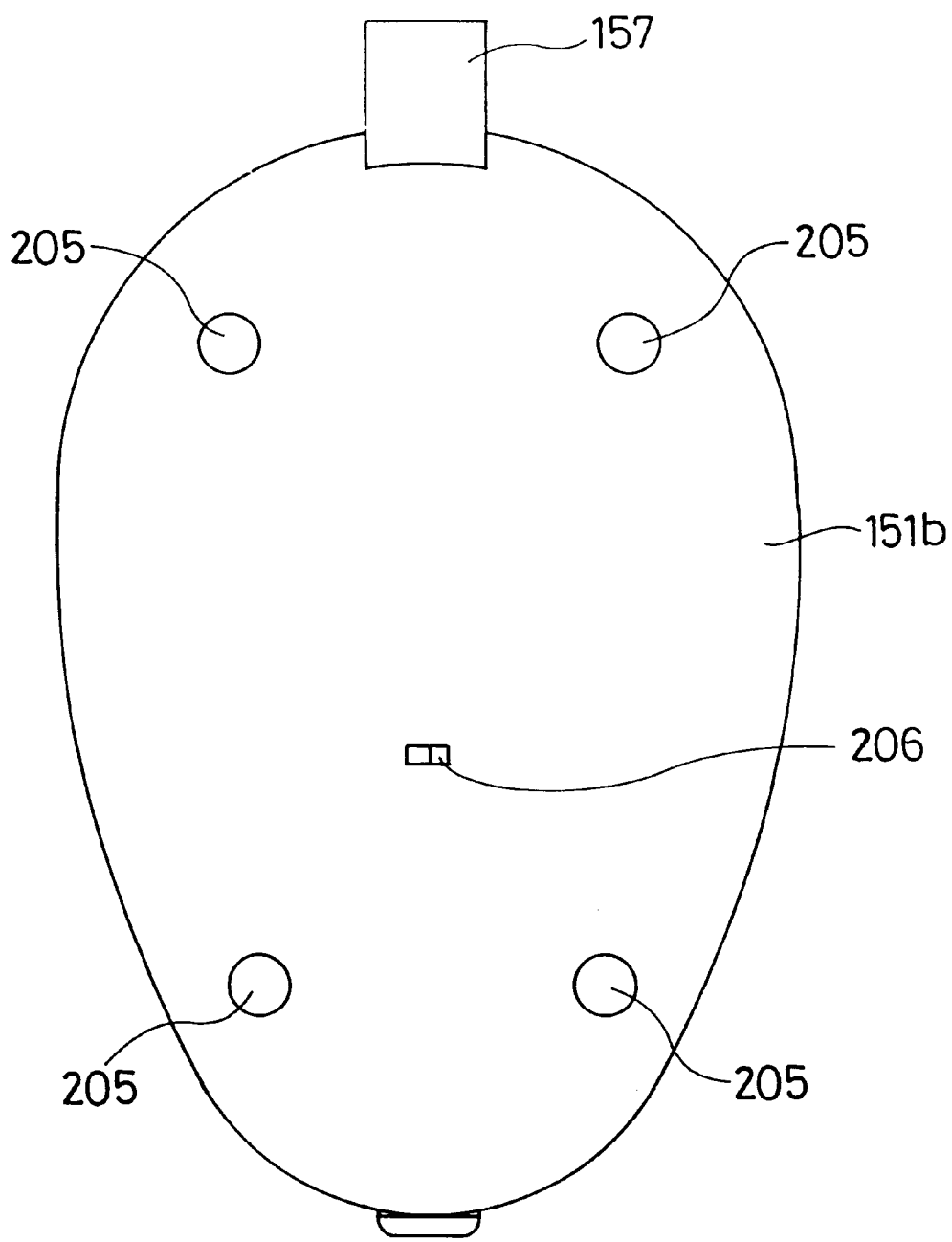
FIG. 26 is a bottom view showing the detecting section of the second embodiment of the present invention.

Also, four rubber feet 205 for prevention of slippage and an operation piece of a slide switch 206 for the power supply protrude from the bottom surface of the lower housing 151 as shown in FIG. 26. The height of the rubber feet 205 are designed to be larger than that of the operation piece.

Here, the slide switch 206 is for turning on/off the electric power to be supplied to the light source section 111 and the image capturing section 12. If the slide switch is mounted on the upper housing 151, the operation piece will be an obstacle when the person to be inspected mounts a hand on the housing 151, so that it is provided at this position.

THIRD EMBODIMENT

Figure 32:
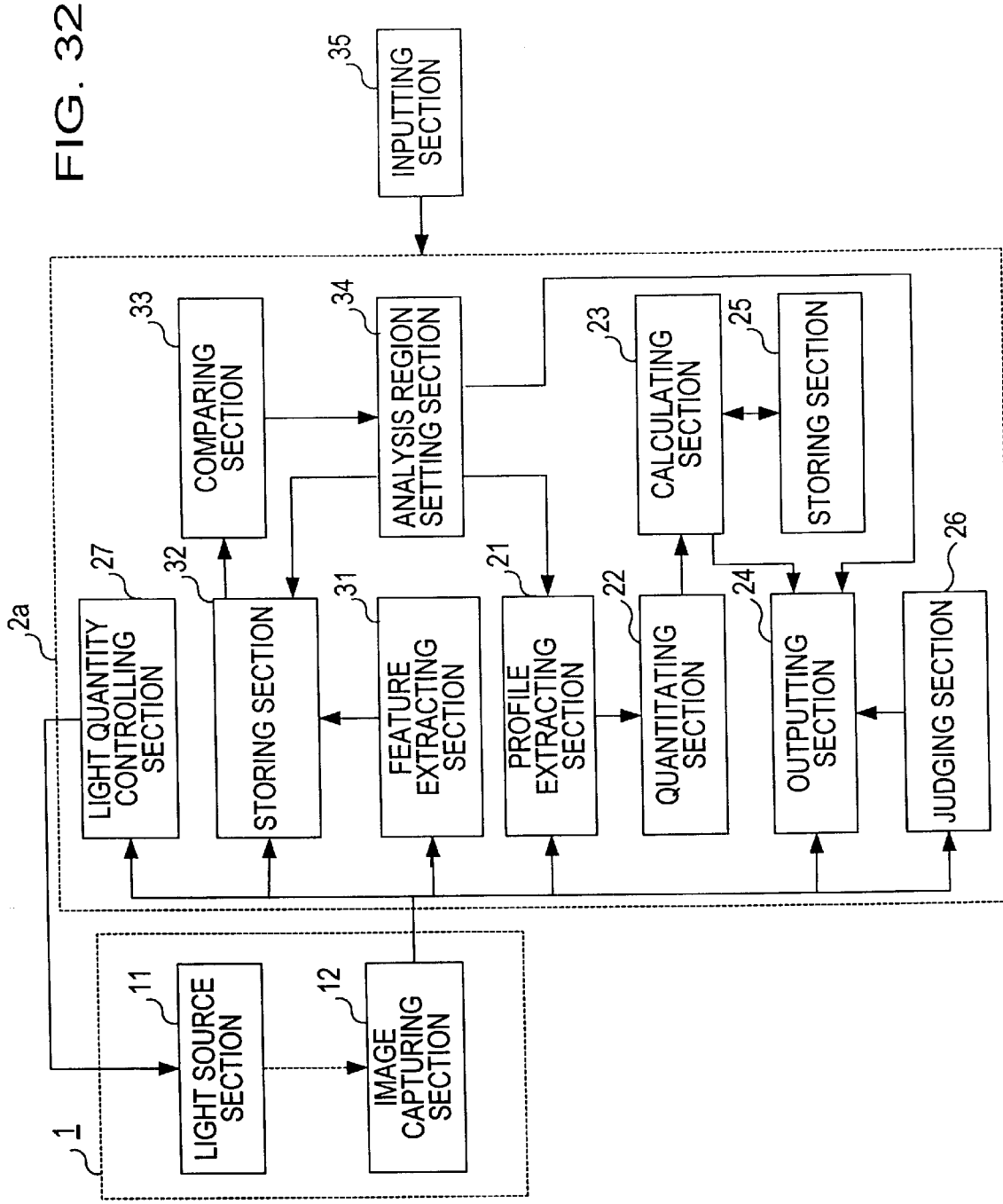
FIG. 32 is a block diagram showing a construction of a detecting section and an analyzing section of a third embodiment of the present invention.

FIG. 32 is a block diagram showing a construction of a third embodiment of a detecting section and an analyzing section of the present invention. Referring to FIG. 32, the analyzing section 2a includes a judging section 26 and a light quantity controlling section 27 in addition to the elements in the analyzing section 2 (FIG. 1) of the first embodiment. Besides the added elements, like numerals denote like elements shown in FIG. 1.

In the case where a finger (middle finger) of a human hand is an object of detection as a part of a living body in the same manner as in the first and second embodiments, it is preferable that the analysis region R1 (FIG. 14) is set at a joint portion or its neighborhood because, at the joint portion, a blood vessel is present near the surface of the skin and it is easy to capture an image.

For that purpose, in this embodiment, a preliminary step is conducted before carrying out the measurement work (FIG. 12) of the first or second embodiment. Namely, the judging section 26 judges whether or not the joint portion is appropriately positioned with respect to the image capturing area of the image capturing section 12 when the person to be inspected mounts the finger F on the detecting section 1. If it is not in an appropriate position, the judging section 26 outputs to the outputting section 24 to that effect so as to communicate it to the person to be inspected and prompts the person to mount the finger correctly.

Further, in this preliminary step, the light quantity controlling section 27 performs an appropriate feedback control of the light quantity of the light source section 11 or 111 on the basis of the image information acquired from the image capturing section 12 so as to perform a light quantity adjustment.

Next, the operations of the judging section 26 and the light quantity controlling section 27 are detailed with reference to the flowchart shown in FIG. 33.

Figure 34:
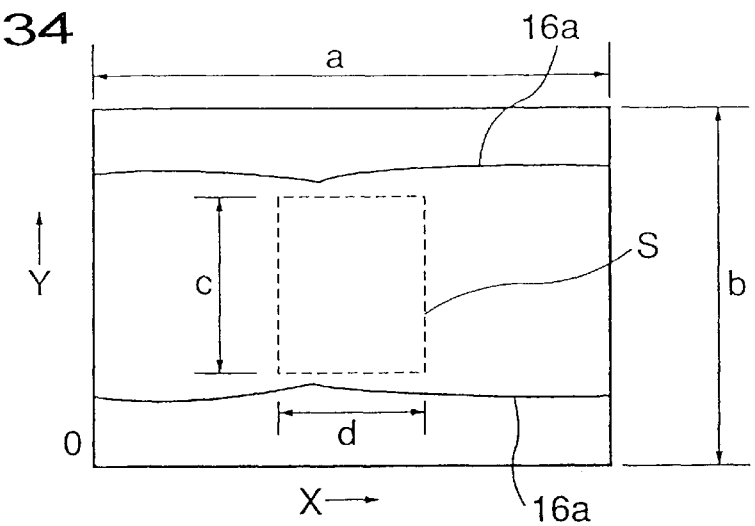
FIG. 34 is an explanatory view showing a region for judging average brightness in an image obtained by the third embodiment of the present invention.

When the person to be inspected mounts a finger on the detecting section 1 at the beginning of the measurement shown in FIG. 12, the operator first operates the inputting section 35 to irradiate the finger by the light source section 11 or 111 to capture an image, whereby the image of the finger having a contour 16a is obtained on a screen of a (640 pixels)×b (480 pixels) as shown in FIG. 34. Therefore, the judging section 26 judges whether or not the difference between the average brightness Q of the total pixels within a judgment region S (c (352 pixels)×d (240 pixels)) set beforehand at the central portion of the image area and the standard value $Q_0$ is larger than a predetermined value $\delta_1$ (step S53). If the difference between Q and $Q_0$ is $\delta^1$ or more, the light quantity controlling section 27 performs rough adjustment of light quantity by controlling the driving current supplied to LED 11a or 11b until the difference becomes smaller than $\delta_1$ (steps S57, S52, S53).

Figure 35:
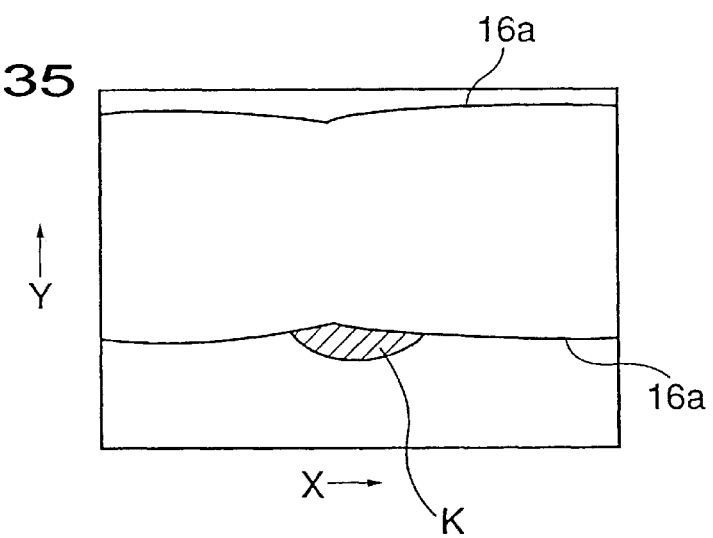
FIG. 35 is an explanatory view showing an example in which a leak light image is present in the image obtained by the third embodiment of the present invention.

Incidentally, when the person to be inspected mounts the finger on the detecting section 1, a portion of the light of the light source section 11 or 111 leaks from a gap between the sidewall members 55, 56 or 155, 156 and the finger if the finger is shifted from an appropriate position in the direction perpendicular to its longitudinal direction, i.e. in the right and left directions, so that a highly bright leak light image K as shown in FIG. 35 appears in the image obtained from the image capturing section 12, thereby forming an obstacle against appropriate image analysis.

Accordingly, the judging section 26 detects the presence or absence of the leak light image K through the following process (step S54).

Figure 36:
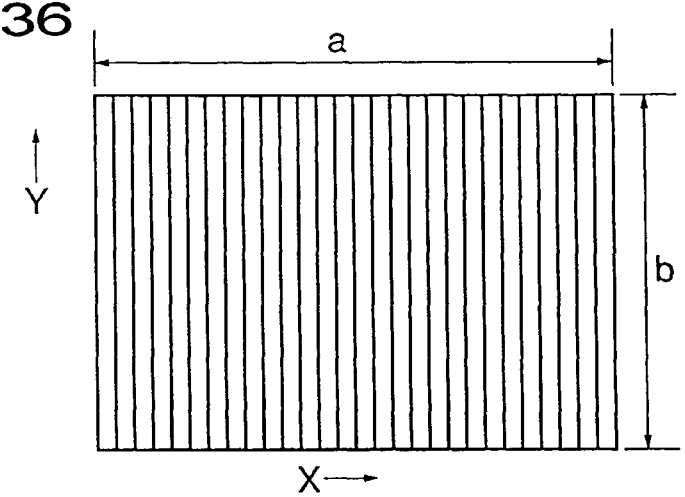
FIG. 36 is an explanatory view showing a method for detecting the leak light image by the third embodiment of the present invention.
Figure 37:
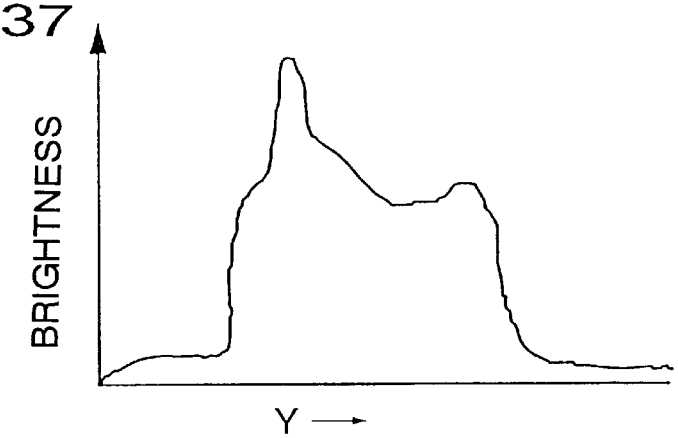
FIG. 37 is an explanatory view showing an example of a brightness profile of an image obtained by the third embodiment of the present invention.
Figure 38:
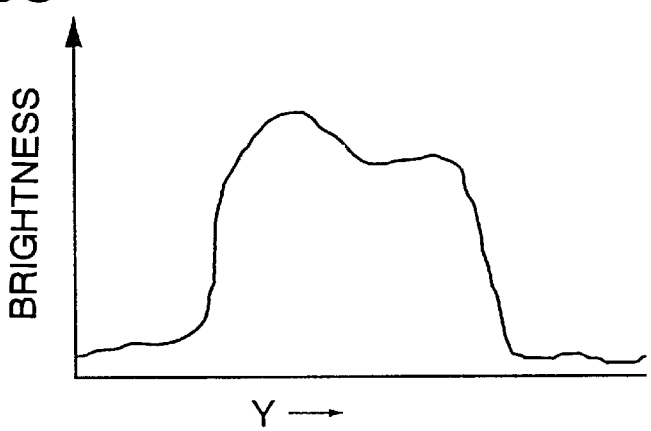
FIG. 38 is an explanatory view showing another example of a brightness profile of an image obtained by the third embodiment of the present invention.

First, each band-like pixel group (8×480 pixels) extending in a Y direction as shown in FIG. 36 is counted as one group for rough partitioning, and a brightness profile along the Y direction is determined for each group. FIG. 37 is an example of a profile when the pixel group traverses the leak light image K, and FIG. 38 is an example of a profile when the pixel group does not traverse the leak light image K. The judging section 26 detects its rising and trailing positions from the obtained profile of each group and connects these points by lines, thereby recognizing them as outer peripheral lines 16b, 16c, respectively, as shown in FIG. 39.

Figure 39:
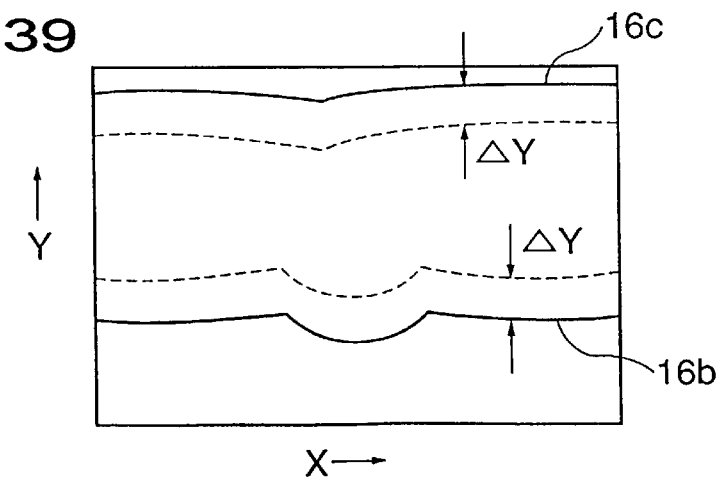
FIG. 39 is an explanatory view showing the method for detecting the leak light image by the third embodiment of the present invention.

Next, an inner region having a width of ΔY pixels is set on the inside of each of the outer peripheral lines 16b, 16c, as shown in FIG. 39 to calculate an average brightness Bf of the two inner regions. When the number of pixels having a higher brightness than Bf×k (where k is a predetermined constant larger than 1) in the two inner regions exceeds a predetermined number, the judging section judges that the leak light image K is present, namely, the light from the light source section 11 or 111 is leaking and is directly incident into the image capturing section 12 (step S54).

When the leak light image K is detected, the judging section 26 can detect a shift of the finger in the right and left directions, so that the judging section 26 allows the outputting section 24 to output a message such as "Please place the finger more to the right" or "Please place the finger more to the left" or "please draw the finger out and insert it again" in accordance with the result of the detection (step S58).

Figure 40:
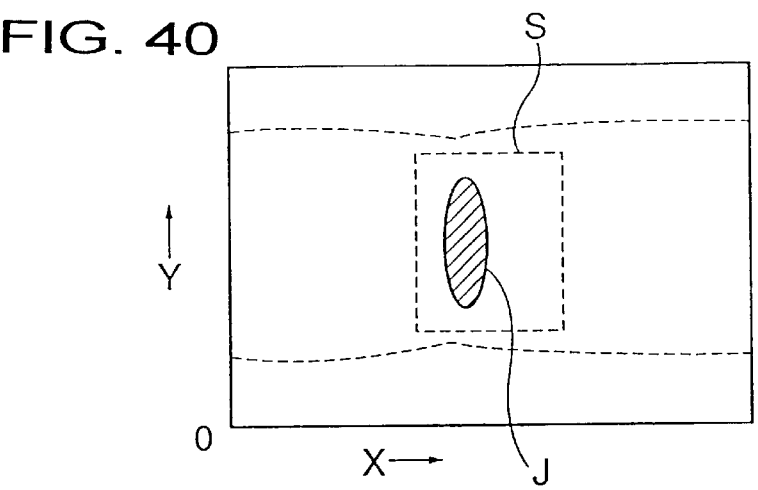
FIG. 40 is an explanatory view showing an example of an image of a joint portion obtained by the third embodiment of the present invention.

When the leak light image K is not detected in the step S54, the judging section 26 judges whether the joint portion is present within the region S (FIG. 34) (step S55). Since the joint portion J has a higher brightness than the other portions of the image as shown in FIG. 40, its position can be easily differentiated through the following process.

Figure 41:
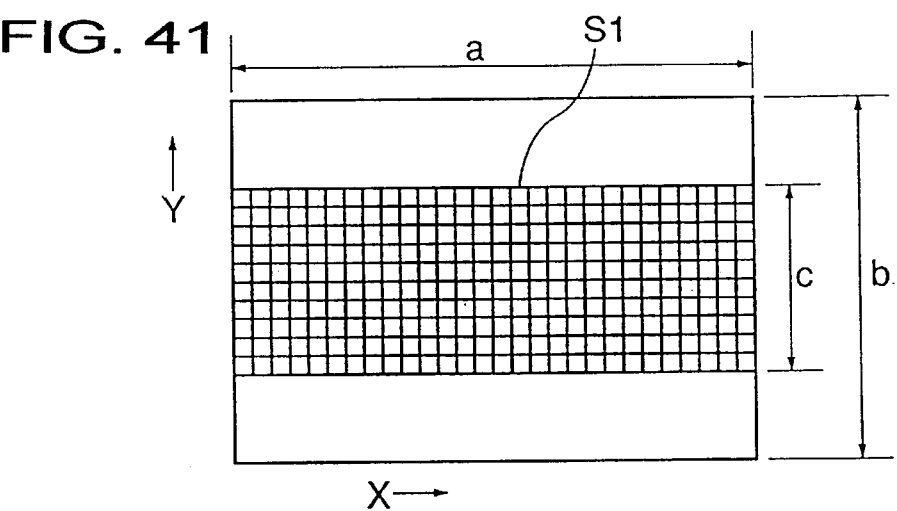
FIG. 41 is an explanatory view showing pixel groups of a region in which the joint portion is searched for in the third embodiment of the present invention.

Namely, the judging section 26 sets a search region S1 of length a and width c (352 pixels) in the whole image region (a×b) as shown in FIG. 41 and performs rough partitioning by counting 8×8 pixels in the search region S1 as one group. The judging section 26 calculates an average brightness of the pixels in each group and detects the position of a group having the maximum average brightness as the position of the joint portion J.

Figure 42:
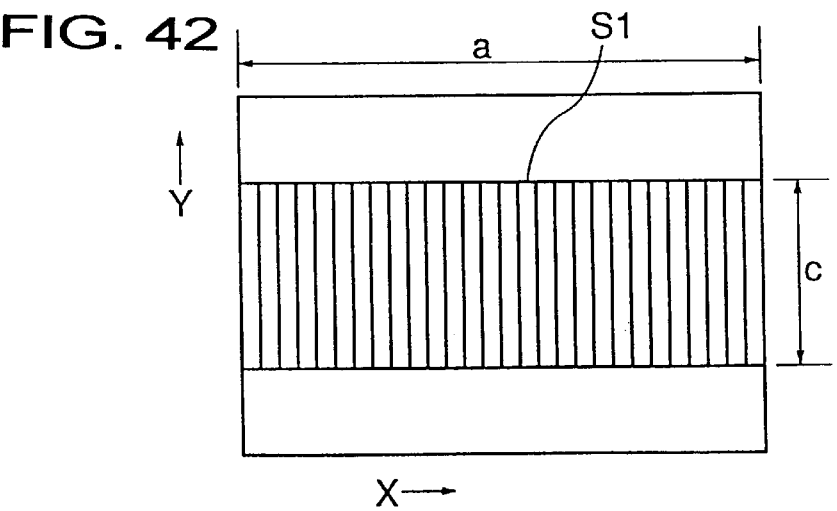
FIG. 42 is an explanatory view showing pixel groups of the region in which the joint portion is searched for in the third embodiment of the present invention.

Also, the judging section 26 may perform rough partitioning of the search region S1 as shown in FIG. 42 by counting each band-like pixel group (8×352 pixels) extending in a Y direction as one group, calculate an average brightness of the pixels in each group, and detect the position of a group having the maximum brightness as the position (X coordinate position) of the joint portion J.

Here, due to the irradiation property or the like of the light source section 11 or 111, the position of the joint position J searched for as above by the judging section 26 may be shifted a little from the actual position of the joint portion. In such a case, the judging section 26 may calculate the true position of the joint portion by substituting the position of the joint portion J searched for as above in a suitable correction function.

Further, if the joint portion J is out of the region S (FIG. 34), the judging section 26 allows the outputting section 24 to output a message such as "Please place it more deeply" or "Please place it more to the front" (step S59).

Also, if the joint portion J is within the region S in the step S55, the judging section 26 allows the region S of FIG. 34 to be shifted in a direction parallel to the X axis so that the X coordinate of the position of the joint portion J comes to its center, and judges whether the difference between an average brightness Q of the total pixels within the shifted region S and a standard value $Q_0$ is larger than a predetermined value $\delta_2$ or not (step S56).

If the difference between Q and $Q_0$ is $\delta_2$ or more, the light quantity controlling section 27 performs fine adjustment of light quantity by controlling a driving current supplied to the LED 11a or 11b until the difference becomes smaller than $\delta_2$ (steps S60, S61, S56).

In this way, when the judging section 26 judges that the mounted state of the finger and the light quantity of the light source are appropriate, the measurement work shown in FIG. 12 is started as shown in the first or second embodiment. The subsequent work is similar to that of the first or second embodiment, so that an explanation is omitted.

Figure 33:
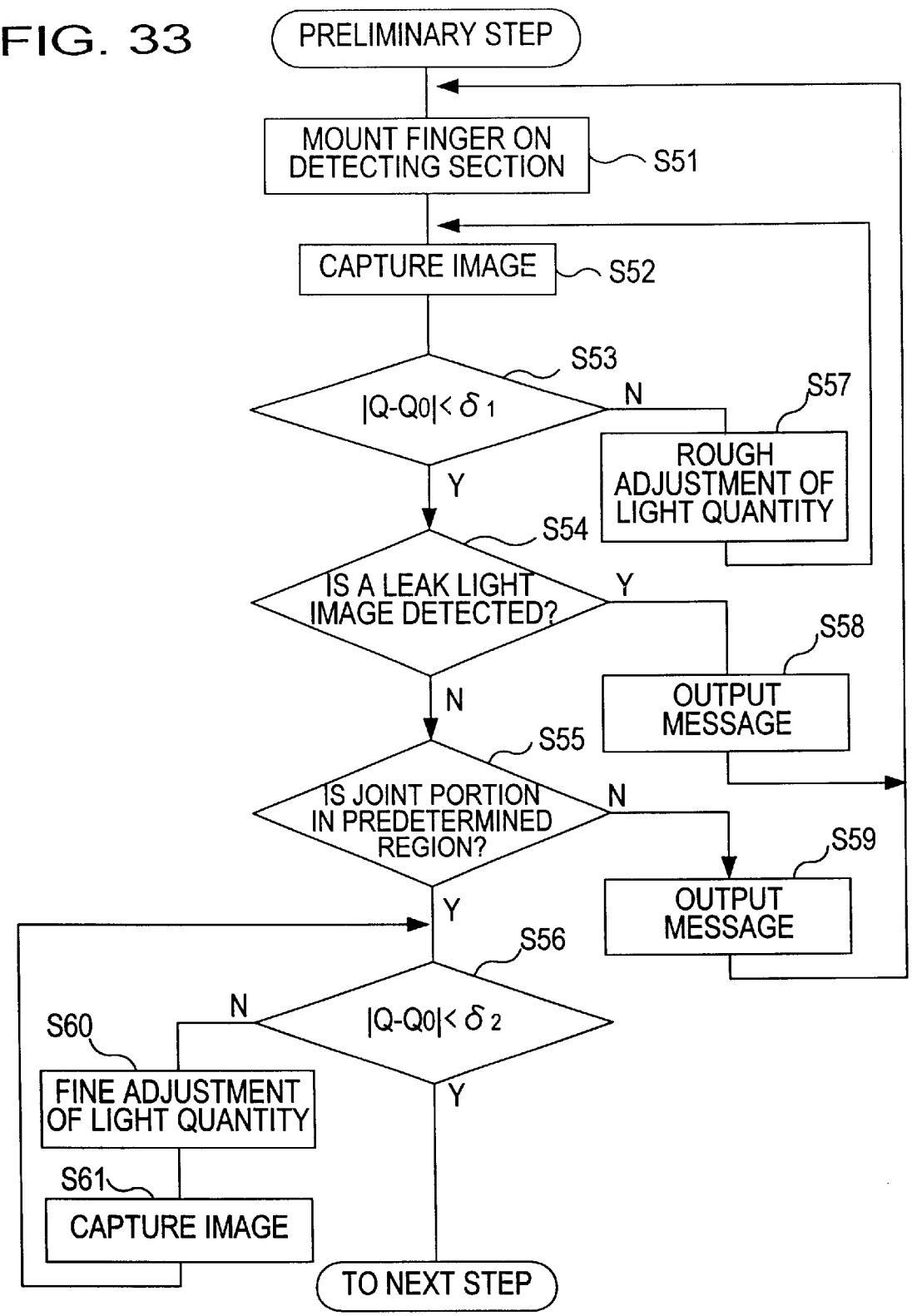
FIG. 33 is a flowchart showing an operation of the detecting section and the analyzing section of the third embodiment of the present invention.

Here, in the measurement work of FIG. 12, the step shown in FIG. 33 is inserted before each of the steps S2, S12, and S13. If the step of FIG. 33 is inserted before the step S2 or S12, the image capture in the step S52 is carried out using the first wavelength. If the step of FIG. 33 is inserted before the step S13, the image capture in the step S52 is carried out using the second wavelength.

Also, a speaker may be provided at the outputting section 24 so as to output a message by sound or voice in the steps S58 and S59.

INDUSTRIAL APPLICABILITY

According to the present invention, since a part of a living body which is an object of measurement can be stably fixed without strain, it is possible to obtain accurate inspection results with good reproducibility.

What is claimed is:

1. An apparatus for living body inspection, comprising:
a base for mounting a portion of a living body to be inspected;
a pair of opposing sidewall members, said sidewall members being distinct from and separated from each other, each sidewall member being pivotally supported by said base such that the side wall member pivots about a first axis, said side wall members being capable of holding the portion of the living body therebetween from both sides thereof;
a cover member pivotally supported by said base such that said cover member pivots about a second axis substantially perpendicular to the first axis;
a light source section for supplying a light to the portion of the living body held on the base and between the sidewall members; and
a light receiving section for detecting optical information from the mounted portion of the living body supplied with the light.

2. The apparatus for living body inspection of claim 1, wherein the sidewall members are urged to approach each other.

3. The apparatus for living body inspection of claim 1, wherein the base member includes a supporting member for supporting the sidewall members such that the sidewall members are movable to approach each other, and an urging member for urging the sidewall members toward each other.

4. The apparatus for living body inspection of claim 3, wherein the supporting member includes a hinge mechanism, and the urging member includes a spring.

5. The apparatus for living body inspection of claim 1, wherein the sidewall members are urged to generate a force component which presses the portion of the living body toward the base with the sidewall members holding the portion of the living body.

6. The apparatus for living body inspection of claim 1, wherein the base is formed such that at least a part of a surface of the base conforms to a morphology of the portion of the living body to be mounted.

7. The apparatus for living body inspection of claim 1, wherein the optical information is information on a blood vessel and blood flowing through the blood vessel.

8. The apparatus for living body inspection of claim 1, wherein the portion of the living body to be inspected is one of a finger and thumb of a human hand; the base has a surface shape conformable to a curved surface formed by the fingers, the thumb, and a palm; and the sidewall members protrude from the base such that the sidewall members hold the one of the finger and thumb to be inspected therebetween from both sides thereof when the fingers, the thumb, and the palm are mounted on the base.

9. The apparatus for living body inspection of claim 8, wherein the base includes at least one recess for positioning the one of the finger and thumb on an upper surface thereof.

10. The apparatus for living body inspection of claim 8, wherein the one of the finger and thumb is a middle finger.

11. The apparatus for living body inspection of claim 10, wherein the base includes a plurality of recesses for positioning the middle finger and adjacent fingers thereof on an upper surface thereof.

12. The apparatus for living body inspection of claim 1, wherein the cover member opposes said base and covers an upper part of the portion of the living body held between the sidewall members.

13. The apparatus for living body inspection of claim 12, wherein the light source section is disposed in the cover member, and the light receiving section is disposed below the base to receive the light transmitted through the portion of the living body from the light source via an opening disposed in the base.

14. The apparatus for living body inspection of claim 1, wherein the light source includes a LED, and the light receiving section includes a CCD.

15. The apparatus for living body inspection of claim 1, wherein each of the sidewall members includes an elastic member in contact with the portion of the living body.

16. The apparatus for living body inspection of claim 1, further comprising:
a light transmitting member in contact with the portion of the living body held between the two sidewall members, and the light source section supplies the light to the living body through the light transmitting member.

17. The apparatus for living body inspection of claim 1, wherein the light receiving section includes an image capturing element.

18. A non-invasive blood analyzer, comprising:
an analyzing section for calculating information on blood flowing through a blood vessel by analyzing an image of a tissue including the blood vessel obtained by an apparatus for living body inspection, said apparatus including,
a base for mounting a portion of a living body to be inspected,
a pair of opposing sidewall members, said sidewall members being distinct from and separated from each other, each side wall member being pivotally supported by said base such that the side wall member pivots about a first axis said side wall member being capable of holding the portion of the living body therebetween from both sides thereof,
a cover member pivotally supported by said base such that said cover member pivots about a second axis substantially perpendicular to the first axis;
a light source section for supplying a light to the portion of the living body held on the base and between the sidewall members, and
a light receiving section for detecting optical information from the mounted portion of the living body supplied with the light, the light receiving section including an image capturing element; and
an outputting section for outputting the calculated information.

19. The non-invasive blood analyzer of claim 18, further comprising:
an inputting section for inputting an analysis condition, wherein the analyzing section analyzes the obtained image of the tissue including the blood vessel on the basis of the input analysis condition.

20. The non-invasive blood analyzer of claim 18, wherein the information on blood is information on hemoglobin concentration and hematocrit.

21. The non-invasive blood analyzer of claim 18, further comprising;
a judging section for judging a mounting state of the portion of the living body relative to the base on the basis of the image obtained by the apparatus for capturing an image of a living body; and
a message outputting section for outputting an instruction message based on the mounting state judged by the judging section.

22. A non-invasive blood analyzer, comprising:
an analyzing section for calculating information on blood flowing through a blood vessel by analyzing an image of a tissue including the blood vessel obtained by an apparatus for living body inspection, said apparatus including,
a base for mounting a portion of a living body to be inspected,
sidewall members holding a mounted portion of the living body therebetween from both sides thereof, said sidewall members being distinct from and separated from each other,
a light source section for supplying a light to the portion of the living body held on the base and between the sidewall members, and
a light receiving section for detecting optical information from the mounted portion of the living body supplied with the light, the light receiving section including an image capturing element;
an outputting section for outputting the calculated information; and a light quantity controlling section for controlling a quantity of the light of the light source section on the basis of image information obtained by the image capturing element.

23. An apparatus for living body inspection, comprising:
a base for mounting a portion of a living body to be inspected;
a pair of opposing sidewall members, each sidewall member being pivotally supported by said base such that the side wall member pivots about a first axis, said side wall members being capable of holding the portion of the living body therebetween from both sides thereof;
a cover member pivotally supported by said base such that said cover member pivots about a second axis substantially perpendicular to the first axis;
a light source section for supplying a light to the portion of the living body held on the base and between the sidewall members; and
a light receiving section for detecting optical information from the mounted portion of the living body supplied with the light,
wherein the base member includes a supporting member for supporting the sidewall members such that the sidewall members are movable to approach each other, and an urging member for urging the sidewall members toward each other.

24. The apparatus for living body inspection of claim 23, wherein the supporting member includes a hinge mechanism, and the urging member includes a spring.

25. The apparatus for living body inspection as claimed in claim 1, wherein the base has a top surface and each sidewall member has a bottom edge surface directly connected to the top surface of the base.

* * * * *